US009918479B2

United States Patent
Asolkar et al.

(10) Patent No.: US 9,918,479 B2
(45) Date of Patent: Mar. 20, 2018

(54) **CONTROL OF PHYTOPATHOGENIC MICROORGANISMS WITH *PSEUDOMONAS* SP. AND SUBSTANCES AND COMPOSITIONS DERIVED THEREFROM**

(71) Applicant: Marrone Bio Innovations, Inc., Davis, CA (US)

(72) Inventors: Ratnakar Asolkar, Davis, CA (US); Ana Lucia Cordova-Kreylos, Davis, CA (US); Carly Todd, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 0 days.

(21) Appl. No.: 14/376,696

(22) PCT Filed: Feb. 27, 2013

(86) PCT No.: PCT/US2013/028112
§ 371 (c)(1),
(2) Date: Oct. 8, 2014

(87) PCT Pub. No.: WO2013/130680
PCT Pub. Date: Sep. 6, 2013

(65) Prior Publication Data
US 2015/0030577 A1    Jan. 29, 2015

Related U.S. Application Data

(60) Provisional application No. 61/604,507, filed on Feb. 28, 2012, provisional application No. 61/670,624, filed on Jul. 30, 2012.

(51) Int. Cl.
*A01N 63/00* (2006.01)
*A01N 63/02* (2006.01)
(Continued)

(52) U.S. Cl.
CPC .............. *A01N 63/00* (2013.01); *A01N 37/06* (2013.01); *A01N 37/36* (2013.01); *A01N 43/08* (2013.01);
(Continued)

(58) Field of Classification Search
None
See application file for complete search history.

(56) References Cited

U.S. PATENT DOCUMENTS 4,542,097 A    9/1985  Labows, Jr. et al.
4,560,656 A    12/1985 Farbood et al.
(Continued)

FOREIGN PATENT DOCUMENTS

GB    1409321 A       8/1975
JP    2009-502965 A   1/2009
(Continued)

OTHER PUBLICATIONS

Stutz ("Naturally Occurring Fluorescent Pseudomonads involved in Suppression of Black Root Rot of Tobacco" Phytopathology, 1986, vol. 76, No. 2, p. 181-185).*
(Continued)

*Primary Examiner* — Robert J Yamasaki
*Assistant Examiner* — Charles Zoltan Constantine
(74) *Attorney, Agent, or Firm* — Ying-Horng Liu; Chainey P. Singelton

(57) ABSTRACT

Provided are compounds and compositions derived from *Pseudomonas* sp., particularly, *Pseudomonas fluorescens* or *Pseudomonas protegens* and more particularly strain having the identifying characteristics of *Pseudomonas* ATCC 55799 having antimicrobial properties and particularly, antibacterial properties.

3 Claims, 10 Drawing Sheets

(51) Int. Cl.
| | |
|---|---|
| A01N 37/06 | (2006.01) |
| A01N 37/36 | (2006.01) |
| C07G 99/00 | (2009.01) |
| C12P 1/04 | (2006.01) |
| A01N 43/08 | (2006.01) |
| C12P 7/64 | (2006.01) |
| C12P 17/04 | (2006.01) |

(52) U.S. Cl.
CPC ............ *A01N 63/02* (2013.01); *C07G 17/00* (2013.01); *C12P 1/04* (2013.01); *C12P 7/6409* (2013.01); *C12P 17/04* (2013.01)

(56) References Cited

U.S. PATENT DOCUMENTS

| | | | |
|---|---|---|---|
| 5,527,525 | A | 6/1996 | Wilson et al. |
| 6,194,194 | B1 | 2/2001 | Molloy |
| 6,451,565 | B1 | 9/2002 | Rabenhorst et al. |
| 7,129,067 | B2 | 10/2006 | Mitsuhashi et al. |
| 2004/0234629 | A1 | 11/2004 | Nakazato et al. |
| 2010/0266717 | A1 | 10/2010 | Asolkar et al. |
| 2011/0021358 | A1 | 1/2011 | Huang et al. |
| 2012/0121745 | A1 | 5/2012 | Rackl et al. |
| 2013/0121978 | A1 | 5/2013 | Asolkar et al. |
| 2013/0196013 | A1 | 8/2013 | Asolkar et al. |

FOREIGN PATENT DOCUMENTS

| | | | |
|---|---|---|---|
| KR | 10-0130075 | B1 | 4/1998 |
| KR | 100519469 | B1 * | 10/2005 |
| WO | WO 91/00012 | | 1/1991 |
| WO | WO 93/00816 | | 1/1993 |
| WO | WO 94/08904 | | 4/1994 |
| WO | 2007/014372 | A2 | 2/2007 |
| WO | WO 2007/031565 | | 3/2007 |
| WO | WO/2008/012756 | | 1/2008 |
| WO | WO/2008/665451 | | 6/2008 |
| WO | WO 2008/130558 | | 10/2008 |
| WO | 2010/123894 | A2 | 10/2010 |
| WO | WO 2013/130680 | | 9/2013 |

OTHER PUBLICATIONS

Abouseoud, M., "Biosurfactant Production from Olive Oil from *Pseudomonas fluorescens*," *Communicating Current Research and Educational Topics and Trends in Applied Microbiology* p. 340-347 (2007).

Abouseoud, M. et al., "Evaluation of Different Carbon and Nitrogen Sources in Production of Biosurfactant by *Pseeudomonas fluorescens*," *Desalination* 223:143-151 (2008).

Aguedo, M. et al., "Mechanisms Underlying the Toxicity of Lactone Aroma Compounds Towards the Producing Yeast Cells," *Journal of Applied Microbiology* 94:258-265 (2003).

Andersson, R.E. et al., "Lipase Production, Lipolysis, and Formation of Volatile Compounds by *Pseudomonas fluorescens* in Fat Containing Media," *Journal of Food Science* 45:1694-1701 (1980).

Asolkar, R., et al. "Daryamides A-C, weakly cytotoxic polyketides from a marine-derived actinomycete of the genus *Streptomyces* strain CNO-085." J. Nat. Prod. 69: 1756-1759. 2006.

Bangera, G.M. et al., "Identification and Characterization of a Gene Cluster for Synthesis of the Polyketide Antibiotic 2,4-Diacetylphloroglucinol from *Pseudomonas fluorescens* Q-287," *Journal of Bacteriology* 181(10):3155-3163 (1999).

Barrasa, J.L.M. et al., "Antibacterial Susceptibility Patterns of Pseudonomas Strains Isolated from Chronic Canine Otitis Externa," *Journal of Vetirenary Medicine* B 47: 191-196 (2000).

Baum, M.M. et al., "Characterization of Structures in Biofilms Formed by a *Pseudomonas fluorescens* Isolated From Soil," *BMC Microbiology* 9:103 (2009).

Bejarano, A. et al., "Bioavailability of the Organophosphorous Insecticide Chlorpyrifos to the Suspension-Feeding Bivalve, Mercenaria Mercenaria, following Exposure to Dissolved and Particulate Matter." *Environmental Toxicology and Chemistry*, vol. 22, No. 9. (2003).

Blumer, C. et al., "Global GacA-Steered Control of Cyanide and Exoprotease Production in *Pseudomonas fluorescens* Involves Specific Ribosome Binding Sites," *PNAS* 96(24):14073-14078 (1999).

Burgess, J.G. et al., "The Development of a Marine Natural Product-Based Antifouling Paint," Biofouling 19(Supplement):197-205 (2003).

Chalier, P. et al., "Enantiodifferentiation of Four γ-Lactones Produced by *Penicillium roqueforti*," *Chirality* 10:786-790 (1998).

Chapalain, A. et al., "Comparative Study of 7 Fluorescent Pseudomonad Clinical Isolates," *Canadian Journal of Microbiology* 54:19-27 (2008).

Choi, H.J. et al., "Involvement of Epidermal Growth Factor Receptor-Linked Signaling Responses in Pseudomonas fluorescens-Infected Alveolar Epithelial Cells," *Infection and Immunity* 79(5):1998-2005 (2011).

Dietz, T.H. et al., "Osmotic and Ionic Regulation of North American Zebra Mussels (*Dreissena polymorpha*)," *American Zoologist* 36:364-372 (1996).

Domenech, C.E. et al., "*Pseudomonas aeruginosa* Cholinesterase and Phosphorylcholine Phosphatase: Two Enzymes Contributing to Corneal Infection," *FEMS Microbiology Letters* 82:131-136 (1991).

El-Sayed, K.A. et al., "Characterization of the Mupirocin Biosynthesis Gene Cluster from *Pseudomonas fluroescens* NCIMB 10586," *Chemistry & Biology* 10:419-430 (2003).

Furukawa, H. et al., "Ferulic Acid Production from Clove Oil by *Pseudomonas fluorescens* E188," *Journal of Bioscience and Bioengineering* 96(4):404-405 (2003).

Gershman, M.D. et al., "Multistate Outbreak of *Pseudomonas fluorescens* Bloodstream Infection after Exposure to Contaminated Heparinized Saline Flush Prepared by a Compounding Pharmacy," *Clinical Infectious Diseases* 47:1372-1379 (2008).

Gibb, A.P. et al., "Rate of Growth of *Pseudomonas fluorescens* in Donated Blood," *Journal of Clincal Pharmacology* 48:717-718 (1995).

Gimmestad, M. et al., "The *Pseudomonas fluorescens* AlgG Protein, but Not Its Mannuronan C-5-Epimerase Activity, Is Needed for Alginate Polymer Formation," *Journal of Bacteriology* 185(12):3515-3523 (2003).

Ekelund, R. et al., "Influence of Suspended Solids on Bioavailability of Hexachlorobenzene and Lindane to the Deposit-Feeding Marine Bivalve, Abra nitida (Muller)" Bulletin of Envionmental Contamination and Toxicology, vol. 38, No. 3, (1987).

Hinsa, S.M. et al., "Biofilm Formation by *Pseudomonas fluorescens* WCS365: A Role for LapD," *Microbiology* 152:1375-1383 (2006).

Howell, C.R. et al., "Suppression of Pythium ultimum-Induced Damping-Off of Cotton Seedlings by *Pseudomonas fluorescens* and its Antibiotic, Pyoluteorin," *Phytopathology* 70(8):712-715 (1980).

Hsueh, P. et al., "Outbreak of *Pseudomonas fluorescens* Bacteremia Among Oncology Patients," *Journal of Clinical Microbiology* 36:(10):2914-2917 (1998).

Ishihara, K. et al., "Effective Production of *Pseudomonas fluorescens* Lipase by Semi-Batch Culture with Turbidity-Dependent Automatic Feeding of Both Olive Oil and Iron Ion," *Applied Microbiology and Biotechnology* 31:45-48 (1989).

Jackson, M.K. et al., "Necrotizing Hepatitis in Pet Birds Associated with *Pseudomonas fluorescens*," *Avian Diseases* 40:473-476 (1996).

Jiang, Y. et al., "High Poly(β-hydroxybutyrate) Production by *Pseudomonas fluorescens* A2a5 from Inexpensive Substrates," *Enzyme and Microbial Technology* 42:167-172 (2008).

Koka, R. et al., "Isolation and Characterization of a Protease from *Pseudomonas fluorescens* R098," *Journal of Applied Microbiology* 89:280-288 (2000).

Kramer, K.J.M. et al., "The 'Musselmonitor®' as Biological Early Warning System, The First Decade," in *Biomonitors and Biomarkers as Indicators of Environmental Change 2, Environmental Science Research* 56:59-87 (2000).

(56) References Cited

OTHER PUBLICATIONS

Liao, C. et al., "Biochemical and Genetic Characterization of an Extracellular Protease from *Pseudomonas fluorescens* CY091," *Applied and Environmental Microbiology* 64(3):914-921 (1998).

Mackie, G.L. et al., "Comparative Biology of Zebra Mussels in Europe and North America: An Overview," *American Zoologist* 36:244-258 (1996).

Madi, A. et al., "The Clinical Pseudomonas fluorescens MFN1032 Strain Exerts a Cytotoxic Effect on Epithelial Intestinal Cells and Induces Interleukin-8 via the AP-1 Signaling Pathway," *BMC Microbiology* 10:215 (2010).

Madi, A. et al., "*Pseudomonas fluorescens* Alters Epithelial Permeability and Translocates Across Caco-2/TC7 Intestinal Cells," *Gut Pathogens* 2:16 (2010).

Manfredi, R. et al., "*Pseudomonas* Organisms Other than *Pseudomonas aeruginosa* as Emerging Bacterial Pathogens in Patients with Human Immunodeficiency Virus Infection," *Infectious Diseases in Clinical Practice* 9:79-87 (2000).

McMahon, R.F., "The Physiological Ecology of the Zebra Mussel, *Dreissena polymorpha*, in North America and Europe," *American Zoologist* 36:339-363 (1996).

Mills, E.L. et al., "A Review of the Biology and Ecology of Quagga Mussel (*Dreissena bugensis*), a Second Species of Freshwater Dreissenid Introduced to North America," *American Zoologist* 36:271-286 (1996).

Mizobuchi, S. et al., "Antifouling Substances Against the Mussel in an Octocoral *Dendronephthya* sp.," *Nippon Suisan Gakkaishi* 59(7):1195-1199 (1993).

Molloy, D.P., "The Potential for Using Biological Control Technologies in the Management of *Dreissena* Spp.," *J. Shellfish Res.* 17:177-183 (1998).

Molloy, D.P. et al., "Overview of a Novel Green Technology: Biological Control of Zebra and Quagga Mussels with *Pseudomonas fluorescens*," *Bacterial Project Overview* 6:1-9 (2007).

Molloy, D.P., "Environmentally Safe Control of Zebra Mussel Fouling," Technical Report (R41909R09) retrieved from the internet at http://www.netl.doe.gov/technologies/coalpower/ewr/pubs/NT41909_NY%20Dept%20of%20Educ_Final%20Report.pdf (May 21, 2008).

Molloy, D.P. et al., "Mode of Action of *Pseudomas fluorescens* Strain CL145A, a Lethal Control Agent of Dreissenid Mussels (Bivalvia: Dreissenidae)," *J. Invertebrate Pathology* 113:115-121 (2013).

Nowak-Thompson, B. et al., "Characterization of the Pyoluteorin Biosynthetic Gene Cluster of *Pseudomonas fluorescens* Pf-5," *Journal of Bacteriology* 181(7):2166-2174 (1999).

Oliveira, M.D. et al., "Forecasting the Expansion of the Invasive Golden Mussel *Llmnoperna fortune* in Brazilian and North American Rivers Based on its Occurrence in the Paraguay River and Pantanal Wetland of Brazil," *Aquatic Invasions* 5:59-73 (2010).

Parente, A.M. et al., "Ultrastructural Aspects of Autolysis of *Pseudomonas fluorescens* Induced by Osmotic Shock," *Journal of General Microbiology* 130:1459-1470 (1984).

Peighami-Ashnaei, S. et al., "Interaction of Different Media on Production and Biocontrol Efficacy of *Pseudomonas fluorescens* P-35 and *Bacillus subtilis* B-3 Against Grey Mold of Apple," *Journal of Plant Pathology* 91(1):65-70 (2009).

Peyer, S.M. et al., "Zebra Mussels Anchor Byssal Threads Faster and Tighter than Quagga Mussels in Flow," *The Journal of Experimental Biology* 212:2027-2036 (2009).

Prabakaran, G. et al., "Isolation of a *Pseudomonas fluorescens* Metabolite/Exotoxin Active Against Both Larvae and Pupae of Vector Mosquitoes," *Pest Management Science* 59:21-24 (2002).

Prabakaran, G. et al., "Development of Cost-Effective Medium of the Large-Scale Production of a Mosquito Pupicidal Metabolite from *Pseudomonas fluorescens* Migula," *Biological Control* 48:264-266 (2009).

Rajmohan, S. et al., "Enzyme from Isolates of *Pseudomonas fluorescens* Involved in Food Spoilage," *Journal of Applied Microbiology* 93:205-213 (2002).

Ramette, A. et al., "*Pseudomas protegens* sp. nov., Widespread Plant-Protecting Bacteria Producing the Biocontrol Compounds 2,4-Diacetylphloroglucinol and Pyoluteorin," *Systematic and Applied Microbiology* 34:180-188 (2011).

Ricciardi, A., "Global Range Expansion of the Asian Mussel *Limnoperna fortunei* (Mytilidae): Another Fouling Threat to Freshwater Systems," *Biofouling* 13(2):97-106 (1998).

Rochu, D. et al., "Purification, Molecular Characterization and Catalytic Properties of *Pseudomonas fluorescens* Enzyme Having Cholinesterase-Like Activity," *Biochemica et Biophysica Acta* 1385:126-138 (1998).

Rossignol, G. et al., "Involvement of a Phospholipase C in the Hemolytic Activity of a Clinical Strain of *Pseudomonas fluorescens*," *BMC Microbiology* 8:189 (2008).

Seo, S-T et al., "Characterization of an Antibacterial Substance Produced by *Erwinia carotovora* subsp. *carotovora* Ecc 32," *J. Gen. Plant Pathol.* 70:273-277 (2004).

Shao, Y.Y. et al., "Chemical constituents of *Antrodia camphorata* submerged whole broth." Nat. Prod. Res. 22: 1151-1157. 2008.

Silby, M.W. et al., "*Pseudomonas* Genomes: Diverse and Adaptable," *FEMS Microbiology Reviews* 35:652-680 (2011).

Silverman, H. et al., "Gill Structure in Zebra Mussels: Bacterial-Sized Particle Filtration," *American Zoologist* 36:373-384 (1996).

Sugiura, M. et al., "Purification, Crystallization and Properties of Triacylglycerol Lipase from *Pseudomonas fluorescens*," *Biochimica et Biophysica Acta* 488:353-358 (1977).

Tan, K.H. et al., "Effect of Culture Conditions on Batch Growth of *Pseudomonas fluorescens* on Olive Oil," *Applied Microbiology and Biotechnology* 23:27-32 (1985).

Tan, K.H. et al., "Utilization of Substrates During Batch Growth of *Pseudomonas fluorescens* on Olive Oil, Lard, and Mutton Tallow," *Applied Microbiology and Biotechnology* 26:443-446 (1987).

Thomashow, L.S. et al., "Role of a Phenazine Antibiotic from *Pseudomonas fluorescens* in Biological Control of *Gaeumannomyces graminis* var. *tritici*," *Journal of Bacteriology* 170(8):3499-3508 (1988).

Veron, W. et al., "Natriuretic Peptides Modify *Pseudomonas fluorescens* Cytotoxicity by Regulating Cyclic Nucleotides and Modifying LPS Structure," *BMC Microbiology* 8:114 (2008).

Von Graevenitz, A. et al., "Pathogenic Significance of *Pseudomonas fluorescens* and *Pseudomonas putida*," *Yale Journal of Biology and Medicine* 44:265-273 (1971).

Wang, S. et al., "Production of Antifungal Materials by Bioconversion of Shellfish Chitin Wastes Fermented by *Pseudomonas fluorescens* K-188," *Enzyme and Microbial Technology* 36:49-56 (2005).

Bangera, G.M. et al., "Identification and Characterization of a Gene Cluster for Synthesis of the Polyketide Antibiotic 2,4-Diacetylphloroglucinol from *Pseudomonas fluorescens* Q2-87," *Journal of Bacteriology* 181(10):3155-3163 (1999).

U.S. Army Corps of Engineers Waterways Experiment Station, "Zebra Mussels: Biology, Ecology, and Recommended Control Strategies," Zebra Mussel Research Technical Note ZMR-1-01, Zebra Mussel Research Program, 9 pages (1995).

U.S. Geological Survey, Florida Caribbean Science Center, "Nonindigenous Species Information Bulletin: Asian Clam, *Corbicula fluminea*," No. 2001-001 (2001).

Wei, B. et al., "*Pseudomonas fluorescens* Encodes the Crohn's Disease-Associated I2 Sequence and T-Cell Superantigen," *Infection and Immunity* 70(12):6567-6575 (2002).

Winson, M.K. et al., "Multiple N-acyl-L-Homoserine Lactone Signal Molecules Regulate Production of Virulence Determinants and Secondary Metabolites in *Pseudomonas aeruginosa*," *PNAS* 92:9427-9431 (1995).

Campbell, P. J. et al., "Integrated biological control of bacterial speck and spot of tomato under Weld conditions using foliar biological control agents and plant growth-promoting rhizobacteria," Biological Control 36 (2006) 358-367.

CN 201380011032.5 Office Action in Chinese dated Jan. 22, 2016.

(56) References Cited

OTHER PUBLICATIONS

Alchihab, Mohamed et al., "Production of γ-Decalactone by a Psychrophilic and a Mesophilic Strain of the Yeast *Rhodotorula aurantiaca*" Appl Biochem Biotechnol (2008) DOI 10.1007/s12010-008-8297-x.
Connelly, N. et al. "Economic Impacts of Zebra Mussels on Drinking Water Treatment and Electric Power Generation Facilities." Environ. Manage 40: 105-112. (2007).
Database CA [Online] Chemical Abstracts Service, Columbus, Ohio, US; Dec. 16, 1998 (Dec. 16, 1998), Al-Shibib, A. et al: "Antimicrobial activity of pyoverdin", XP002742574, retrieved from STN Database accession No. 1998:787676 * abstract * & Al-Shibib, A. et al: "Antimicrobial activity of pyoverdin", Bulletin of Pharmaceutical Sciences, Assiut University, 21(1), 37-40 Coden: BPAUEC; ISSN: 1110-0052, 1998.
Don Cronin et al: "Ecological interaction of a biocontrol Pseudomonas fluorescens strain producing 2,4-diacetylphloroglucinol with the soft rot potato pathogen *Erwinia carotovora* subsp. *atroseptica*", FEMS Microbiology Ecology, vol. 23, No. 2, Jun. 17, 1997 (Jun. 17, 1997), pp. 95-106.
De Villiers et al., "Structure and Activity in Molluscides". Nature, (Mar. 1967).
Dufosse, L. et al., "Chirality of the ylactones produced by Sporidiobolus salmonicolor grown in two different media." Chirality 9:667-671. (1997).
Extended European Search Report EP 13754767-5 dated Aug. 3, 2015.
Gocho, S. et al. "Biotransformation of oleic acid to optically active y-dodecalactone." Biosci. Biotech. Biochem. 59: 1571-1572. (1995).
Guanpeng Gao et al: "Effect of Biocontrol Agent Pseudomonas fluorescens 2P24 on Soil Fungal Community in Cucumber Rhizosphere Using T-RFLP and DGGE", PLOS One, vol. 7, No. 2, Feb. 16, 2012 (Feb. 16, 2012), p. e31806.
Muhammad Nadeem Hassan et al: "Suppression of red rot caused by Colletotrichum falcatum on sugarcane plants using plant growth-promoting rhizobacteria", Biocontrol, Kluwer Academic Publishers, DO, vol. 55, No. 4, Feb. 24, 2010 (Feb. 24, 2010), pp. 531-542.
Hoda H El-Hendawy et al: 11 The biological control of soft rot disease in melon caused by *Erwinia carotovora* subsp. *carotovora* using Pseudomonas fluorescens 11, Microbial. Res., Apr. 1, 1998 (Apr. 1, 1998), pp. 55-60.
Itoh, Y. et al., "A Novel Hepatoprotective y-Lactone, MH-031. I. Disclovery, Isolation, Physico-Chemical Properties and Structural Elucidation," J. Antibiotics 44:832-837 (1991).
Ji P et al: "Integrated biological control of bacterial speck and spot of tomato under field conditions using foliar biological control agents and plant growth-promoting rhizobacteria", Biological Control, San Diego, CA, US, vol. 36, No. 3, Mar. 1, 2006 (Mar. 1, 2006), pp. 358-367.
Karatayev, A.Y. et al., The Effects of Dreissena Polymorpha (Pallas) Invasion on Aquatic Communities in Eastern Europe, J. Shellfish Research 16:187-203 (1997).
Kavino et al: "Induction of systemic resistance in banana (*Musa* spp.) against Banana bunchy top virus (BBTV) by combining chitin with root-colonizing Pseudomonas fluorescens strain CHA0", European Journal of Plant Pathology, Kluwer Academic Publishers, DO, vol. 120, No. 4, Nov. 1, 2007 (Nov. 1, 2007), pp. 353-362.
Kojima, Y. et al., "Purification and Characterization of an Alkaline Lipase from Pseudomonas fluorescens AK102," . Biosci. Biotech. Biochem. 58(9):1564-1568 (1994).
Murty, M.G. et al., "Production of a Mosquitocidal Exotoxin by a Pseudomonas fluorescens Strain," Journal of Invertebrate Pathology 64:68-70 ( 1994).
D. Couillerot et al: "Pseudomonas fluorescens and closely-related fluorescent pseudomonads as biocontrol agents of soil-borne phytopathogens", Letters in Applied Microbiology, vol. 48, No. 5, May 1, 2009 (May 1, 2009), pp. 505-512.

Picot, L. et al., "Pseudomonas fluorescens as a Potential Pathogen: Adherence to Nerve Cells," Microbes and Infection 3:985-995 (2001).
Ramette et al: "Sp. nov., widespread plant-protecting bacteria producing the biocontrol compounds 2,4-diacetylphloroglucinol and pyoluteorin", Systematic and Applied Microbiology, vol. 34, No. 3, Mar. 9, 2011 (Mar. 9, 2011), pp. 180-188.
Sandler, J.S. et al., "Cytotoxic 13-Carbolines and Cyclic Peroxides from the Palauan Sponge *Plakortis nigra*," J. Nat. Prod. 65:1258-1261 (2002).
S Schmoock et al: 11 Biological control of apple scab and fire blight by the application of the non-pathogenic bacterium *Pseudomonas fluorescens* Bk3 to the leaf surface 11 Orgprints, Jan. 1, 2008 (Jan. 1, 2008), pp. 306-309.
Seleim et al: "Biological control of bacterial wilt of tomato by plant growth promoting rhizobacteria", plant pathology ournal, Jan. 1, 2011 (Jan, 1, 2011), pp. 146-153.
Shaaban, K.A. et al., "Eiectrospray Ionization Mass Spectra of Piperazimycins A and B and γ-Butyrolactones from a Marine-Derived *Streptomyces* sp.," J. Antibiot. 61:736-746 (2008).
Stockwell et al: "*Psuedomonas* spp. for Integrated Biological Control", Phytopathology, American Phytopathological Society, US, vol. 97, Feb. 1, 2007 (Feb. 1, 2007), pp. 244-249.
Crosier, D.M. et al., "Golden Mussel—*Limnoperna fortune*," from http://el.erdc.usace.army.mil/ansrp/limnoperna_fortunei.pdf.
Darrigan, G. et al., The Golden Mussel, *Limnoperna fortunei* (Dunker, 1857) (Bivalvia: Mytilidae), in the Neotropical Region: A 10 Year Story of Invasion, Tentacle No. 11:8-9 (2003).
Kisaalita, W.S. et al., "Defined Media for Optimal Pyoverdine Production by Pseudomonas fluorescens 2-79," Applied Microbiology and Biotechnology 39:750-755 (1993).
Rossignol, G. et al., "Phenotypic Variation in the Pseudomonas fluorescens Clinical Strain MFN 1032," Research in Microbiology 160:337-344 (2009).
Brader, G. et al. "Altering Substrate Chain Length Specificity of an Acylhomoserine Lactone Synthase in Bacterial Communication," J. Bioi. Chem. 280:10403-10409 (2005).
Flodgaard, L.R. et al., "Nonbioluminescent Strains of Photobacterium Phosphoreum Produce the Cell-to-Cell Communication Signal N-(3-Hydroxyoctanoyl)homoserine Lactone," Applied and Environmental Microbiology 71:2113-2120 (2005).
Lorenzo, M. et al., "13C NMR-Based Empirical Rules to Determine the Configuration of Fatty Acid Butanolids. Novel y-Dilactones from *Pterogorgia* spp," Organic Letters 8:5001-5004 (2006).
Macisaac, H.J., "Potential Abiotic and Biotic Impacts of Zebra Mussels on the Inland Waters of North America," Amer. Zoo/. 36:287-299 (1996).
Miller, S.L. et al., "Axinellamide, a New Alkaloid from the Marine Sponge *Axinella* Sp.," Tetrahedron Letters 36:5851-5852 (1995).
Perry, K. et al., "Detecting Physiological and Pesticide-Induced Apoptosis in Early Developmental Stages of Invasive Bivalves," Hydrobio/ogia 628:153-164 (2009).
Rezanka, T. et al., "y-Lactones from the Soft Corals *Sarcophyton trochehophorum* and *Lithophyton arboreum*," Tetrahedron 57:8743-8749 (2001).
Ricciardi, A. et al., "Impending Extinctions of North American Freshwater Mussels (*Unionoida*) Following the Zebra Mussel (*Dreissena polymorpha*) Invasion," J. Animal Ecology 67:613-619 (1998).
Shen, Y-C. et al., "Novel Linear C22-Sesterterpenoids from Sponge *Ircinia formosana*," Tetrahedron Letters 47:4007-4010 (2006).
Vieira, P.C. et al., "y-Lactones from *Iryanthera* Species," Phytochemistry 22:711-713 (1983).
Couillerot, O. et al. "Pseudomonas fluorescens and closely-related fluorescent pseudomonads as biocontrol agents of soil-borne phytopathogens" Letters in Applied Microbiology 48 (May 2009) 505-512.
Gao, Guanpeng et al. "Effect of Biocontrol Agent Pseudomonas fluorescens 2P24 on Soil Fungal Community in Cucumber Rhizosphere Using T-RFLP and DGGE" PLoS ONE (Feb. 2012) 7(2): e31806. doi:10.1371/journal.pone.0031806.

(56) References Cited

OTHER PUBLICATIONS

El-Hendawy, Hoda H. et al. "The biological control of soft rot disease in melon caused by *Erwinia carotovora* subsp. *carotovora* using Pseudomonas fluorescens" Microbial. Res. (Apr. 30, 1998) 153, 55-60.

Stockwell, Virginia O. et al. "Using *Pseudomonas* spp. for Integrated Biological Control" Phytopathology (Feb. 2007) 97:244-249.

Seleim, M.A.A. et al. "Biological Control of Bacterial Wilt of Tomato by Plant Growth Promoting Rhizobacteria" Plant Pathology Journal (2011) 10 (4): 146-153.

Abed, Hannane et al., "Screening for Pseudomonas and Bacillus antagonistic rhizobacteria strains for the biocontrol of Fusarium wilt of chickpea" Eurasian J Soil Sci 2016, 5 (3) 182-191.

Nagarajkumar, M. et al., "Involvement of secondary metabolites and extracellular lytic enzymes produced by Pseudomonas fluorescens in inhibition of Rhizoctonia solani, the rice sheath blight pathogen." Microbiological Research, Apr. 30, 2004, vol. 159, No. 1, pp 73-81.

Tymiak, A. A., et al., "Structure of obafluorin: An antibacterial β-lactone from Pseudomonas fluorescens." The Journal of Organic Chemistry, Dec. 1985, vol. 50, No. 26, pp. 5491-5495.

Bangera, Gita. M., et al., "Characterization of a Genomic locus Required for Synthesis of the Antibiotic 2,4-diacetylphloroglucinol by the Biological Control Agent Pseudomonas fluorescens Q2-87." Molecular Plant-Microbe Interactions , Mar. 1996, vol. 9, No. 2, pp. 83-90.

\* cited by examiner

1

2

SEQUENCE LISTING

```
<160> NUMBER OF SEQ ID NOS: 5

<210> SEQ ID NO 1
<211> LENGTH: 20
<212> TYPE: DNA
<213> ORGANISM: Unknown
<220> FEATURE:
<223> OTHER INFORMATION: Synthetic oligonucleotide, Forward Primer FD1
      5' - 3'

<400> SEQUENCE: 1
agagtttgat cctggctcag                                                    20

<210> SEQ ID NO 2
<211> LENGTH: 17
<212> TYPE: DNA
```

<210> SEQ ID NO 2
<211> LENGTH: 17
<212> TYPE: DNA
<213> ORGANISM: Unknown
<220> FEATURE:
<223> OTHER INFORMATION: synthetic oligoncleotide, Reverse Primer RD1, 5' - 3'

<400> SEQUENCE: 2
aaggaggtga tccagcc    17

<210> SEQ ID NO 3
<211> LENGTH: 1216
<212> TYPE: DNA
<213> ORGANISM: Unknown
<220> FEATURE:
<223> OTHER INFORMATION: synthetic oligonucleotide, CL145A (ATCC 55799) FD1 Forward Sequence

<400> SEQUENCE: 3

```
catgcaagtc gagcggcagc acgggtactt gtacctggtg gcgagcggcg gacgggtgag      60
taatgcctag gaatctgcct agtagtgggg gataacgtcc ggaaacgggc gctaataccg     120
catacgtcct acgggagaaa gtgggggatc ttcggacctc acgctattag atgagcctag     180
gtcggattag ctagttggtg aggtaatggc tcaccaaggc gacgatccgt aactggtctg     240
agaggatgat cagtcacact ggaactgaga cacggtccag amtcctacgg gaggcagcag     300
tggggaatat tggacaatgg gcgaaagcct gatccagcca tgccgcgtgt gtgaagaagg     360
tcttcggatt gtaaagcact ttaagttggg aggaagggca gttacctaat acgtgattgt     420
tttgacgtta ccgacagaat aagcaccggc taactctgtg ccagcagccg cggtaataca     480
gagggtgcaa gcgttaatcg gaattactgg gcgtaaagcg cgcgtaggtg gtttgttaag     540
ttggatgtga aagccccggg ctcaacctgg gaactgcatc caaaactggc aagctagagt     600
atggtagagg gtggtggaat ttcctgtgta gcggtgaaat gcgtagatat aggaaggaac     660
accagtggcg aaggcgacca cctggactga tactgacact gaggtgcgaa agcgtgggga     720
gcaaacagga ttagataccc tggtagtcca cgccgtaaac gatgtcaact agccgttggg     780
agccttgagc tcttagtggc gcagctaacg cattaagttg accgcctggg gagtacggcc     840
gcaaggttaa aactcaaatg aattgacggg ggcccgcaca agcggtggag catgtggttt     900
aattcgaagc aacgcgaaga accttaccag gccttgacat ccaatgaact ttctagagat     960
agattggtgc cttcgggaca ttgagacagg tgctgcatgg ctgtcgtcag ctcgtgtcgt    1020
gagatgttgg ttaagtccgt acgagcgcac ccttgtctag ttacagcacg tatggtkggc    1080
actctagaga ctgcgtgaca acggagaaag gkggatgacg tcagtcatca tgcctacgcc    1140
tgggctacca cgtgctacat gtcggtacag gttgcaagcc gargkgacta atccataaat    1200
cgatcgtagt ccggac                                                    1216
```

<210> SEQ ID NO 4
<211> LENGTH: 1146
<212> TYPE: DNA
<213> ORGANISM: Unknown
<220> FEATURE:
<223> OTHER INFORMATION: synthetic oligonucleotide, CL145A (ATCC 55799) RD1 Reverse Sequence Listing

<400> SEQUENCE: 4

```
gttcgacttc ccccagtcat gaatcacacc gtggtaaccg tcctcccgaa ggttagacta      60
gctacttctg gtgcaaccca ctcccatggt gtgacgggcg gtgtgtacaa ggcccgggaa     120
cgtattcacc gcgacattct gattcgcgat tactagcgat tccgacttca cgcagtcgag     180
```

```
ttgcagactg cgatccggac tacgatcggt tttatgggat tagctccacc tcgcggcttg    240
gcaacccttt gtaccgacca ttgtagcacg tgtgtagccc aggccgaaag ggccatgatg    300
acttgacgtc atccccacct tcctccggtt tgtcaccggc agtctcctta gagtgcccac    360
cataacgtgc tggtaactaa ggacaagggt tgcgctcgtt acgggactta acccaacatc    420
tcacgacacg agctgacgac agccatgcag cacctgtctc aatgttcccg aaggcaccaa    480
tctatctcta gaaagttcat tggatgtcaa ggctggtaa ggttcttcgc gttgcttcga     540
attaaaccac atgctccacc gcttgtgcgg gccccgtca attcatttga gttttaacct    600
tgcggccgta ctccccaggc ggtcaactta atgcgttagc tgcgccacta agagctcaag    660
gctcccaacg gctagttgac atcgtttacg gcgtggacta ccagggtatc taatcctgtt    720
tgctccccac gctttcgcac ctcagtgtca gtatcagtcc aggtggtcgc cttcgccact    780
ggtgttcctt cctatatcta cgcatttcac cgctacacag gaaattccac caccctctac    840
catactctag cttgccagtt ttggatgcag ttcccaggtt gagcccgggg ctttcacatc    900
caacttaaca aaccacctac gcgcgcttta cgcccagtaa ttccgattaa cgcttgcacc    960
ctctgtatta ccgcggctgc tgggcacaga gttagccggt gcttatttct gtcggtacgt   1020
caaaacatca cgtattaggt aactgccctt ctccacttaa agtgctttac atcgagactc   1080
tcacacacgc gcatgctgga gaaatcagct ttcgccattg gtccaatatt ccccactgct   1140
gcttcg                                                              1146

<210> SEQ ID NO 5
<211> LENGTH: 1445
<212> TYPE: DNA
<213> ORGANISM: Unknown
<220> FEATURE:
<223> OTHER INFORMATION: synthetic oligonucleotide, CL145A (ATCC 55799)
      Consensus Sequence

<400> SEQUENCE: 5
catgcaagtc gagcggcagc acgggtactt gtacctggtg gcgagcggcg gacgggtgag     60
taatgcctag gaatctgcct agtagtgggg gataacgtcc ggaaacgggc gctaataccg    120
catacgtcct acgggagaaa gtgggggatc ttcggacctc acgctattag atgagcctag    180
gtcggattag ctagttggtg aggtaatggc tcaccaaggc gacgatccgt aactggtctg    240
agaggatgat cagtcacact ggaactgaga cacggtccag amtcctacgg gaggcagcag    300
tggggaatat tggacaatgg gcgaaagcct gatccagcca tgccgcgtgt gtgaagaagg    360
tcttcggatt gtaaagcact ttaagttggg aggaagggca gttacctaat acgtgattgt    420
tttgacgtta ccgacagaaa taagcaccgg ctaactctgt gcccagcagc cgcggtaata    480
cagagggtgc aagcgttaat cggaattact gggcgtaaag cgcgcgtagg tggtttgtta    540
agttggatgt gaaagccccg ggctcaacct gggaactgca tccaaaactg gcaagctaga    600
gtatggtaga gggtggtgga atttcctgtg tagcggtgaa atgcgtagat ataggaagga    660
acaccagtgg cgaaggcgac cacctggact gatactgaca ctgaggtgcg aaagcgtggg    720
gagcaaacag gattagatac cctggtagtc cacgccgtaa acgatgtcaa ctagccgttg    780
ggagccttga gctcttagtg gcgcagctaa cgcattaagt tgaccgcctg gggagtacgg    840
ccgcaaggtt aaaactcaaa tgaattgacg gggcccgca caagcggtgg agcatgtggt    900
ttaattcgaa gcaacgcgaa gaaccttacc aggccttgac atccaatgaa ctttctagag    960
atagattggt gccttcggga acattgagac aggtgctgca tggctgtcgt cagctcgtgt   1020
```

```
cgtgagatgt tgggttaagt cccgtaacga gcgcaaccct tgtccttagt taccagcacg    1080
ttatggtggg cactctaagg agactgccgg tgacaaaccg gaggaaggtg gggatgacgt    1140
caagtcatca tggccctttc ggcctgggct acacacgtgc tacaatggtc ggtacaaagg    1200
gttgccaagc cgcgaggtgg agctaatccc ataaaaccga tcgtagtccg gatcgcagtc    1260
tgcaactcga ctgcgtgaag tcggaatcgc tagtaatcgc gaatcagaat gtcgcggtga    1320
atacgttccc gggccttgta cacaccgccc gtcacaccat gggagtgggt tgcaccagaa    1380
gtagctagtc taaccttcgg gaggacggtt accacggtgt gattcatgac tggggaagt    1440 cgaac                                                                1445
```

CONTROL OF PHYTOPATHOGENIC MICROORGANISMS WITH *PSEUDOMONAS* SP. AND SUBSTANCES AND COMPOSITIONS DERIVED THEREFROM

The instant application is a 35 U.S.C. § 371 application of PCT/US13/28112 filed on Feb. 27, 2013. The PCT/US13/28112 application claims the benefit under 35 U.S.C. § 119(e) to U.S. provisional applications 61/670,624 filed on Jul. 30, 2012, and 61/604,507 filed on Feb. 28, 2012. The content of all of which are incorporate herein by reference in their entirety.

INCORPORATION OF SEQUENCE LISTING

This instant application contains a Sequence Listing which has been submitted in ASCII format via EFS-Web and is hereby incorporated by reference in its entirety. Said ASCII copy is named MOI-42027-US_ST25.txt and is 6,582 bytes in size.

TECHNICAL FIELD

Compositions and methods for controlling phytopathogenic microorganisms, particularly bacteria and fungi, derived from *Pseudomonas* sp, particularly, *Pseudomonas protogens* are provided.

BACKGROUND

Plant pathogens are responsible for significant losses in agricultural production. Diseases in plants may be caused by bacteria, fungi or viruses.

Most bacterial plant diseases can be controlled with a combination of host resistance, cultural practices, chemical and biological control.

Several strains of *Pseudomonas* have previously demonstrated biocontrol properties (see for example, Dowling and O'Gara, 1994, for discussion of antifungal and antibacterial properties; Keel et al., 1992, for discussion of antibacterial properties, U.S. Pat. Nos. 5,622,846, 5,552,315, Ramette et al., 2011). However, there is no clear understanding regarding the mechanisms of pathogen control. Some theories include the induction of systemic resistance in the host plant, competition with the plant pathogens or the productions of antagonistic compounds against the plant pathogens.

*Pseudomonas* strain CL145A has been isolated from water samples and has a demonstrated ability to control mollusks (see, for example, see Molloy, D. P. U.S. Pat. No. 6,194,194, issued Feb. 27, 2001 and US Patent Application Pub. No. 20100266717).

SUMMARY OF THE INVENTION

Provided are isolated compounds and compositions derived from *Pseudomonas* sp. and particularly from a strain of a *Pseudomonas* species having anti-microbial properties and particularly, antibacterial properties and antifungal properties.

In a particular embodiment, such compounds derived from *Pseudomonas* species have the following characteristics:
(a) is obtainable from a *Pseudomonas* species, particularly, a *Pseudomonas* species which produces at least one compound that controls zebra, quagga and golden mussels;
(b) modulates one or more species of phytopathogenic microorganisms and
(c) has a molecular weight and HPLC retention time selected from the group consisting of:
   (i) a molecular weight of about 300-380 and more particularly, about 324 as determined by Liquid Chromatography/Mass Spectroscopy (LC/MS), has an HPLC retention time of about 12-22 minutes, more specifically about 17 minutes and even more specifically about 17.50 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm; and has a UV absorption at 214, 252, 312 nm;
   (ii) a molecular weight of about 300-360 and more particularly, about 314 as determined by LC/MS; has an HPLC retention time of about 10-20 minutes, more specifically about 15 minutes and even more specifically about 15.23 min with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and has a UV absorption at 299, 311, 325 nm;
   (iii) a molecular weight of about 580-680 and more particularly, about 627 as determined by LC/MS; has an HPLC retention time of about 8-20 minutes, more specifically about 14 minutes and even more specifically about 14-24 min and has a UV absorption at 299, 311, 325 nm.
   (iv) a molecular weight of about 350-425 and more particularly, about 386 as determined by LC/MS; has an HPLC retention time of about 6-16 minutes, more specifically about 9 minutes and even more specifically about 9.06 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm; and has a UV absorption at 221, 267, 361 nm.

In a more particular embodiment, the phytopathogenic microorganism is phytopathogenic bacteria or phytopathogenic fungi. In an even more particular embodiment, phytopathogenic bacteria is a member of at least one of *Bacillus* sp. (e.g., *Bacillus subtilus, Bacillus cereus*) *Xanthomonas* sp. (*Xanthomonas acernea, Xanthomonas albilineans, Xanthomonas alfalfae* ssp. *jlfalfa, Xanthomonas alfalfae* ssp. *citrumelonis, Xanthomonas ampelina, Xanthomonas arboricola* pv. *corylina, Xanthomonas arboricola* pv. *juglandis, Xanthomonas arboricola* pv. *pruni, Xanthomonas axonopodis, Xanthomonas axonopodis* pv. *alfalfa, Xanthomonas axonopodis* pv. *allii, Xanthomonas axonopodis* pv. *anacardii, Xanthomonas axonopodis* pv. *begonia, Xanthomonas axonopodis* pv. *citri, Xanthomonas axonopodis* pv. *citrumelo, Xanthomonas axonopodis* pv. *dieffenbachiae, Xanthomonas axonopodis* pv. *glycines, Xanthomonas axonopodis* pv. *malvacearum, Xanthomonas axonopodis* pv. *manihotis, Xanthomonas axonopodis* pv. *phaseoli, Xanthomonas axonopodis* pv. *poinsettiicola, Xanthomonas axonopodis* pv. *vasculorum, Xanthomonas axonopodis* pv.

*vesicatoria, Xanthomonas axonopodis* pv. *vitians, Xanthomonas begoniae, Xanthomonas campestris, Xanthomonas campestris* pv. *alfalfa, Xanthomonas campestris* pv. *alfalfa, Xanthomonas campestris* pv. *armoraciae, Xanthomonas campestris* pv. *Begonia, Xanthomonas campestris* pv. *campestris, Xanthomonas campestris* pv. *Carotae, Xanthomonas campestris* pv. *coriandri, Xanthomonas campestris* pv. *Corylina, Xanthomonas campestris* pv. *cucurbitae, Xanthomonas campestris* pv. *dieffenbachiae, Xanthomonas campestris* pv. *hederae, Xanthomonas campestris* pv. *hyacinthi, Xanthomonas campestris* pv. *incanae, Xanthomonas campestris* pv. *juglandis, Xanthomonas campestris* pv. *malvacearum, Xanthomonas campestris* pv. *Mangiferaeindicae, Xanthomonas campestris* pv. *musacearum, Xanthomonas campestris* pv. *Oryzae, Xanthomonas campestris* pv. *Oryzicola, Xanthomonas campestris* pv. *Papavericola, Xanthomonas campestris* pv. *pelargonii, Xanthomonas campestris* pv. *Phaseoli, Xanthomonas campestris* pv. *poinsettiicola, Xanthomonas campestris* pv. *Pruni, Xanthomonas campestris* pv. *raphani, Xanthomonas campestris* pv. *Translucens, Xanthomonas campestris* pv. *vasculorum, Xanthomonas campestris* pv. *Vesicatoria, Xanthomonas campestris* pv. *vitians, Xanthomonas campestris* pv. *Zinnia, Xanthomonas citri, Xanthomonas citri* ssp. *citri, Xanthomonas citri* ssp. *malvacearum, Xanthomonas cucurbitae, Xanthomonas euvesicatoria, Xanthomonas fragariae, Xanthomonas fuscans* ssp. *fuscans, Xanthomonas gardneri, Xanthomonas hortorum, Xanthomonas hortorum* pv. *carotae, Xanthomonas hortorum* pv. *hederae, Xanthomonas hortorum* pv. *Pelargonii, Xanthomonas hyacinthi, Xanthomonas maltophilia, Xanthomonas manihotis, Xanthomonas oryzae, Xanthomonas oryzae* pv. *oryzae, Xanthomonas oryzae* pv. *oryzicola, Xanthomonas perforans, Xanthomonas populi, Xanthomonas translucens* pv. *cerealis, Xanthomonas translucens* pv. *graminis, Xanthomonas translucens* pv. *secalis, Xanthomonas translucens* pv. *translucens, Xanthomonas translucens* pv. *undulosa, Xanthomonas vasculorum, Xanthomonas vasicola* pv. *holcicola, Xanthomonas vesicatoria, Xanthomonas vesicatoria* pv. *vesicatoria*), *Streptomyces* (e.g., *Streptomyces scabie, Streptomyces acidiscabies, Streptomyces turgidiscabies, Streptomyces ipomoeae, Streptomyces alkaliscabies*), *Erwinia*, (e.g., *Erwinia carotovora, Erwinia amylovora, Erwinia ananas, Erwinia chrysanthemi, Erwinia aroideae, Erwinia carneigieana, Erwinia cypripedi, Erwinia herbicola, Erwinia nimmipressuralis, Erwinia pyrifoliae, Erwinia rhapontici, Erwinia rubrifaciens, Erwinia salicis, Erwinia tracheiphila*) or *Botrytis* sp. (e.g., *Botrytis cinerea, Botrytis acalda, Botrytis allii* [*botrytis* rot], *Botrytis byssoidea* [mycelial neck rot], *Botrytis convolute, Botrytis alliptica, Botrytis paeoniae, Botrytis porri, Botrytis squamosal, Botrytis tulipae*). Phytopathogenic fungi in a particular embodiment, include but are not limited to, *Sphaerotheca* sp. (*Sphaerotheca delphinii, Sphaerotheca fuliginea, Sphaerotheca fusca, Sphaerotheca macularis, Sphaerotheca mors-uvae, Sphaerotheca pannosa, Sphaerotheca pannosa* var. *rosae, Sphaerotheca phytoptophila*)

Also provided are compositions comprising these compounds and further, methods for obtaining these compounds. In a particular embodiment, these compounds may be obtained by (a) cultivating a culture of *Pseudomonas* species that controls zebra, quagga and golden mussels, under conditions sufficient to produce the compounds set forth above in said cultivated culture and (b) isolating the compound from the cultivated culture of (a).

Further provided is a method of modulating at least one species of a phytopathogenic microorganism in a location with an amount of a cell suspension or whole cell broth comprising cells derived from a *Pseudomonas* species, wherein said *Pseudomonas* species produces one or more substances that control zebra, quagga and golden mussels, or a supernatant, filtrate, cell fraction, one or more metabolites, one or more compounds and/or extract derived therefrom, effective to modulate said phytopathogenic microorganisms. Also provided is the use of an amount of a cell suspension or whole cell broth comprising cells derived from a *Pseudomonas* species, wherein said *Pseudomonas* species produces one or more substances that control zebra, quagga and golden mussels, or a supernatant, filtrate, cell fraction, one or more metabolites, one or more compounds and/or extract derived therefrom to formulate a composition for modulating one or more phytopathogenic microorganisms.

In a particular embodiment, the compound or metabolite may include but is not limited to:

(I) the compounds set forth above;

(II) a compound that (i) has a molecular weight of about 1280-1310 as determined by Liquid Chromatography/Mass Spectroscopy (LC/MS); (ii) has 1H NMR values of δ 9.25, 8.36, 8.06, 7.82, 7.71, 7.52, 7.45, 6.82, 6.36, 6.08, 5.42, 5.39, 5.30, 5.14, 4.68, 4.42, 4.31, 4.16, 4.11, 4.07, 3.95-3.86, 3.83, 3.72, 3.66, 3.53, 3.48, 3.37, 3.17, 3.06, 2.56, 2.53, 2.45, 2.32, 2.21, 2.02, 1.96, 1.84, 1.72, 1.65, 1.61, 1.51, 1.48-1.37, 1.32, 1.12, 0.94, 0.91, 0.68 and (c) has an (High Pressure Liquid Chromatography) (HPLC) retention time of about 50-55 min on a reversed phase C-18 HPLC column using a water: acetonitrile gradient solvent system (0-10 min; 30-40% aqueous $CH_3CN$, 10-20 min; 40-60% aqueous $CH_3CN$, 20-60 min; 60-80% aqueous $CH_3CN$, 60-65 min; 80-100% aqueous $CH_3CN$) at 2.5 mL/min flow rate and UV detection of 210 nm;

(III) a compound that (i) has a molecular weight of about 1310-1335 as determined by LC/MS; (ii) has an HPLC retention time of about 55-60 min on a reversed phase C-18 HPLC column using a water:acetonitrile gradient solvent system (0-10 min; 30-40% aqueous $CH_3CN$, 10-20 min; 40-60% aqueous $CH_3CN$, 20-60 min; 60-80% aqueous $CH_3CN$, 60-65 min; 80-100% aqueous $CH_3CN$) at 2.5 mL/min flow rate and UV detection of 210 nm;

(IV) a compound that (i) has a molecular weight of about 540-550 as determined by LC/MS; (ii) has an HPLC retention time of about 50-55 min on a reversed phase C-18 HPLC column using a water:acetonitrile solvent system (0-10 min; 35-45% aqueous $CH_3CN$, 10-20 min; 45-60% aqueous $CH_3CN$, 20-50 min; 60-85% aqueous $CH_3CN$, 50-60 min; 85-100% aqueous $CH_3CN$, 60-70 min; 100% $CH_3CN$) at 10 mL/min flow rate and UV detection of 210 nm;

(V) compound that is a lactone and has a hydroxylated unsaturated fatty acid lactone structure comprising at least one lactone moiety which is a 5 membered γ-lactone, at least one unsaturated moiety and at least one alcohol group; a molecular weight from 285 to about 310 in the core structure; at least 15 carbons and at least 3 oxygens;

(VI) a compound that has the structure wherein: X are each independently —O, —NR$_1$, or —S, wherein R$_1$ is —H or C$_1$-C$_6$ alkyl; n=0 to 15, R$_2$ to R$_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond or triple bond;

(VII) a compound that has a hydroxylated unsaturated fatty acid structure comprising at least one carboxylic acid moiety, at least one unsaturated moiety and at least one alcohol group; a molecular weight from 285 to about 310 in the core structure; at least 15 carbons and at least 3 oxygens;

(VIII) a compound has the structure

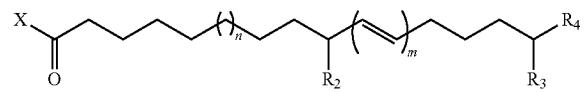

wherein: X are each independently —OH, —NR$_1$, or —S, wherein R$_1$ is —H or C$_1$-C$_6$ alkyl; n=0 to 15, R$_2$ to R$_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond, triple bond;

(IX) a compound that has the structure

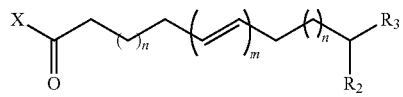

or a acceptable salt or steriosomers thereof, wherein: X are each independently —OH, —NR$_1$, or —S, wherein R$_1$ is —H or C$_1$-C$_6$ alkyl; n=0 to 15, R$_2$, R$_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond, triple bond;

(X) a compound that has the structure

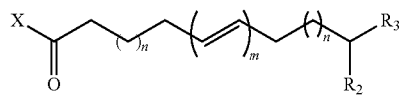

or a acceptable salt or stereoisomers thereof, wherein: X are each independently —OH, —NR$_1$, or —S, wherein R$_1$ is —H or C$_1$-C$_6$ alkyl; n=0 to 15, R$_2$, R$_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=0 to 15, (XI) a compound that has the structure

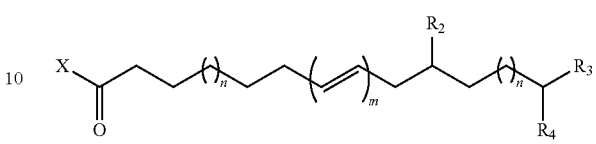

or a acceptable salt or steriosomers thereof, wherein: X are each independently —OH, —NR$_1$, or —S, wherein R$_1$ is —H or C$_1$-C$_6$ alkyl; n=0 to 15, R$_2$ to R$_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond, triple bond;

(XII) a compound that has the structure

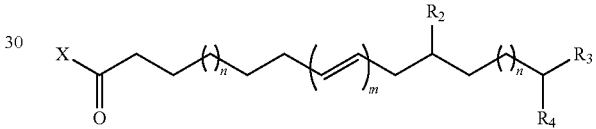

wherein R$_1$ is —H or C$_1$-C$_6$ alkyl; n=0 to 15, R$_2$ to R$_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=0 to 15;

(XIII) a lactone selected from the group consisting of gamma-dodecalactone, delta-tridecalactone, piliferolide A and alpha-heptyl-gamma-butyrolactone and (XIV) a sarmentine analog selected from the group consisting of N-Cyclopentyldecanamide, N-(Decanoyl)pyrrolidine, N-(Decanoyl)piperidine, N-(Decanoyl)hexamethyleneimine, N-Cyclopentyldecenamide, (N-(Decenoyl)pyrrolidine, N-(Decenoyl)piperidine, N-(Decenoyl)hexamethyleneimine and N-(Decenoyl)piperidine;

(XV) 11-hydroxy-12-ene-octadecanoic acid;

(XVI) 9-hexadecenoic acid; and (XVII) ricinoleic acid.

In a particular embodiment, the substances set forth above may be applied to a plant or soil.

Further, the substances set forth above may be applied in combination with an antibiotic, particularly an antibiotic effective against soil-borne bacteria. In a related aspect, provided is a combination comprising the substances set forth above and another antibiotic effective against soil-borne bacteria. These combinations may also be compositions. In a related aspect, also provided is the use of these substances and antibiotics in formulating these combinations. In a further related aspect also provide is the use of these combinations in controlling soil-borne bacteria.

The *Pseudomonas* sp. used in the compositions or methods set forth above or compounds or metabolites set forth above may be derived from *Pseudomonas* sp. that may be selected from the group consisting of *Pseudomonas protegens, Pseudomonas saponiphila, Pseudomonas ficuserectae, Pseudomonas congelans, Pseudomonas tremae, Pseudomonas caricapapayae, Pseudomonas mandelii, Pseudomonas savastanoi, Pseudomonas syringae, Pseudomonas chlororaphis* subsp. *piscium, Pseudomonas cannabina, Pseudomonas marginalis, Pseudomonas simiae, Pseudomonas avellanae, Pseudomonas chlororaphis* subsp. *aurantiaca, Pseudomonas chlororaphis* subsp. *chlororaphis, Pseudomonas frederiksbergensis, Pseudomonas amygdali, Pseudomonas extremaustralis, Pseudomonas kilonensis, Pseudomonas lini, Pseudomonas Antarctica, Pseudomonas corrugata, Pseudomonas poae, Pseudomonas grimontii, Pseudomonas brassicacearum* subsp. *Neoaurantiaca, Pseudomonas meridian, Pseudomonas trivialis, Pseudomonas veronii, Pseudomonas lundensis, Pseudomonas salomonii, Pseudomonas rhodesiae, Pseudomonas arsenicoxydans, Pseudomonas thivervalensis, Pseudomonas deceptionensis, Pseudomonas palleroniana, Pseudomonas chlororaphis* subsp. *aureofaciens, Pseudomonas costantinii, Pseudomonas lurida, Pseudomonas migulae, Pseudomonas orientalis, Pseudomonas extremorientalis, Pseudomonas mediterranea, Pseudomonas brassicacearum* subsp. *brassicacearum, Pseudomonas abietaniphila, Pseudomonas baetica, Pseudomonas brenneri, Pseudomonas psychrophila, Pseudomonas jessenii, Pseudomonas fragi, Pseudomonas tolaasii, Pseudomonas proteolytica, Pseudomonas taetrolens, Pseudomonas mohnii, Pseudomonas moorei, Pseudomonas moraviensis, Pseudomonas gessardii, Pseudomonas cichorii, Pseudomonas libanensis, Pseudomonas benzenivorans, Pseudomonas panacis, Pseudomonas umsongensis, Pseudomonas reinekei, Pseudomonas fluorescens, Pseudomonas agarici, Pseudomonas lutea, Pseudomonas mucidolens, Pseudomonas azotoformans, Pseudomonas viridiflava, Pseudomonas koreensis, Pseudomonas kuykendallii, Pseudomonas synxantha, Pseudomonas segetis, Pseudomonas marincola, Pseudomonas cedrina* subsp. *cedrina, Pseudomonas graminis, Pseudomonas vancouverensis, Pseudomonas cedrina* subsp. *fulgida, Pseudomonas plecoglossicida, Pseudomonas cuatrocienegasensis, Pseudomonas taiwanensis, Pseudomonas putida Pseudomonas rhizosphaerae, Pseudomonas anguilliseptica, Pseudomonas monteilii, Pseudomonas fuscovaginae, Pseudomonas mosselii, Pseudomonas taeanensis, Pseudomonas asplenii, Pseudomonas entomophila, Pseudomonas cremoricolorata, Pseudomonas parafulva, Pseudomonas alcaliphila, Pseudomonas oleovorans* subsp. *lubricantis, Pseudomonas borbori, Pseudomonas composti, Pseudomonas toyotomiensis, Pseudomonas batumici, Pseudomonas flavescens, Pseudomonas vranovensis, Pseudomonas punonensis, Pseudomonas balearica, Pseudomonas indoloxydans, Pseudomonas guineae, Pseudomonas japonica Pseudomonas stutzeri, Pseudomonas seleniipraecipitans, Pseudomonas peli, Pseudomonas fulva, Pseudomonas argentinensis, Pseudomonas xanthomarina, Pseudomonas pohangensis, Pseudomonas oleovorans, Pseudomonas mendocina, Pseudomonas luteola, Pseudomonas straminea, Pseudomonas caeni, Pseudomonas aeruginosa, Pseudomonas tuomuerensis, Pseudomonas azotgens, Pseudomonas indica, Pseudomonas oryzihabitans, Pseudomonas otitidis, Pseudomonas psychrotolerans, Pseudomonas zeshuii, Pseudomonas resinovorans, Pseudomonas oleovorans* subsp. *oleovorans, Pseudomonas thermotolerans, Pseudomonas bauzanensis, Pseudomonas duriflava, Pseudomonas pachastrellae, Pseudomonas citronellolis, Pseudomonas alcaligenes, Pseudomonas xinjiangensis, Pseudomonas delhiensis, Pseudomonas sabulinigri, Pseudomonas litoralis, Pseudomonas pelagia, Pseudomonas linyingensis, Pseudomonas knackmussii, Pseudomonas panipatensis, Pseudomonas nitroreducens, Pseudomonas nitritireducens, Pseudomonas jinjuensis, Pseudomonas pertucinogena, Pseudomonas xiamenensis, Pseudomonas cissicola, Pseudomonas halophile, Pseudomonas boreopolis, Pseudomonas geniculate, Pseudomonas beteli, Pseudomonas hibiscicola, Pseudomonas pictorum, Pseudomonas carboxydohydrogena* In a specific embodiment, the *Pseudomonas* species is *Pseudomonas protogens* or *Pseudomonas fluorescens*. In another particular embodiment, the *Pseudomonas* is a *Pseudomonas* strain having the identifying characteristics of *Pseudomonas* ATCC 55799.

The *Pseudomonas* species or strain in another particular embodiment may have the following identifying characteristics:

(i) enzymatic activity for acid and alkaline phosphatase, leucine arylamidase and naphthol-A5-BI-phosphohydrolase;

(ii) is resistant to tetracycline, erythromycin, streptomycin, penicillin, ampicillin, chromamphenicaol and cefuroxme;

(iii) a 16S rRNA sequence comprising the forward sequence set forth in SEQ ID NO:3, a reverse sequence set forth in SEQ ID NO:4 and a consensus sequence set forth in SEQ ID NO:5;

(iv) contains the fatty acids 17:0, 3OH, 16:0, 1:0, 3OH and (v) produces pyoluteorin and 2,4-diacetylphologlinol.

DETAILED DESCRIPTION

Figure 1:
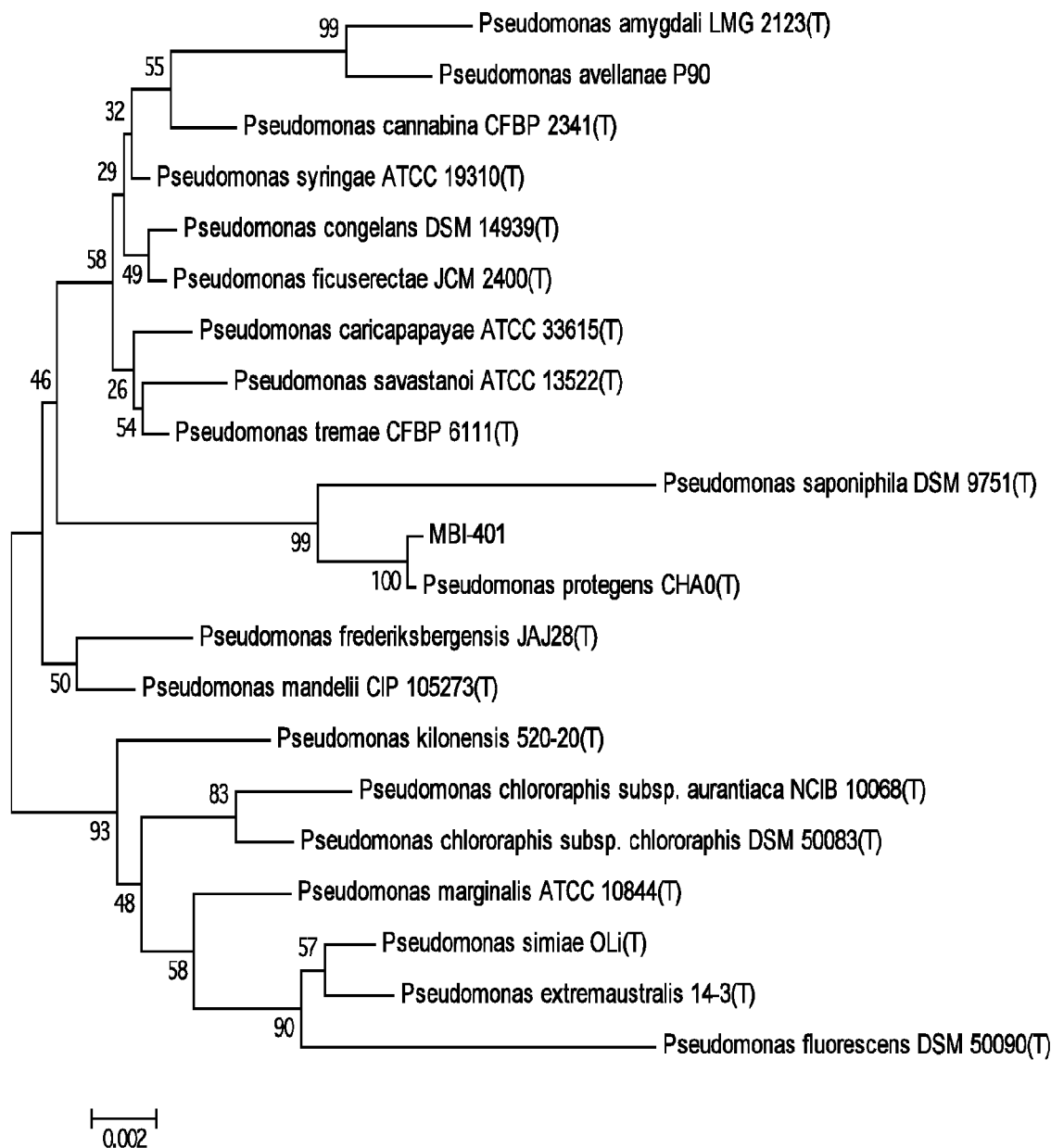
FIG. 1 shows the evolutionary relationships of taxa—A Neighbor-Joining tree to visualize the relationship of CL145A (MBI-401) to the type strains of the genus *Pseudomonas*.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and the include plural references unless the context clearly dictates otherwise. For example, "a substance" also encompasses "substances".

As defined herein, "controlling mussels" means controlling the eggs, larvae, veligers and post-veligers of the mussel by killing or disabling them so that they cannot colonize in a given location.

As defined herein, the term "modulate" is used to mean to alter the amount of phytopathogenic microorganism infestation or rate of spread of phytopathogenic microorganism infestation, or kill, be lethal or toxic to phytopathogenic microorganisms in a location. "Modulate phytopathogenic microorganism infestation" also encompasses modulating the effects of said infestation, which includes but is not limited to disease severity, infection, damage to plant and root tissue, as well as damage to plant fruit, seeds, etc.

As defined herein, "derived from" and "obtainable from" means directly isolated or obtained from a particular source or alternatively having identifying characteristics of a substance or organism isolated or obtained from a particular source. These terms are used interchangeably throughout the specification.

As defined herein, "derived from a *Pseudomonas* species" means a cell broth comprising cells from a *Pseudomonas* species, a cell suspension comprising cells from a *Pseudomonas* species as well as a cell fraction, supernatant, filtrate, extract or compound. The extract may be derived from not only a cell suspension or whole cell broth but also a filtrate, supernatant or fraction derived from said whole cell broth or cell suspension.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods.

Substances

The substances used in the compositions and methods set forth above may be derived from *Pseudomonas* species or strain. As defined herein, "derived from" or "obtainable from" means that a compound may be isolated from or produced by a cell suspension, whole cell broth, filtrate, supernatant, fraction or extract. A compound "produced by" a cell suspension, whole cell broth, filtrate, supernatant, fraction or extract may also be referred to as "a metabolite". The extract may be derived from not only a cell suspension or whole cell broth but also a filtrate, supernatant or fraction derived from said whole cell broth or cell suspension.

In a particular embodiment, the substances are obtainable from a *Pseudomonas* species or strain of a *Pseudomonas* species, which produce compounds that control zebra, quagga and golden mussels. The *Pseudomonas* species include but are not limited to *Pseudomonas protegens, Pseudomonas saponiphila, Pseudomonas ficuserectae, Pseudomonas congelans, Pseudomonas tremae, Pseudomonas caricapapayae, Pseudomonas mandelii, Pseudomonas savastanoi, Pseudomonas syringae, Pseudomonas chlororaphis* subsp. *piscium, Pseudomonas cannabina, Pseudomonas marginalis, Pseudomonas simiae, Pseudomonas avellanae, Pseudomonas chlororaphis* subsp. *aurantiaca, Pseudomonas chlororaphis* subsp. *chlororaphis, Pseudomonas frederiksbergensis, Pseudomonas amygdali, Pseudomonas extremaustralis, Pseudomonas kilonensis, Pseudomonas lini, Pseudomonas Antarctica, Pseudomonas corrugata, Pseudomonas poae, Pseudomonas grimontii, Pseudomonas brassicacearum* subsp. *Neoaurantiaca, Pseudomonas meridian, Pseudomonas trivialis, Pseudomonas veronii, Pseudomonas lundensis, Pseudomonas salomonii, Pseudomonas rhodesiae, Pseudomonas arsenicoxydans, Pseudomonas thivervalensis, Pseudomonas deceptionensis, Pseudomonas palleroniana, Pseudomonas chlororaphis* subsp. *aureofaciens, Pseudomonas costantinii, Pseudomonas lurida, Pseudomonas migulae, Pseudomonas orientalis, Pseudomonas extremorientalis, Pseudomonas mediterranea, Pseudomonas brassicacearum* subsp. *brassicacearum, Pseudomonas abietaniphila, Pseudomonas baetica, Pseudomonas brenneri, Pseudomonas psychrophila, Pseudomonas jessenii, Pseudomonas fragi, Pseudomonas tolaasii, Pseudomonas proteolytica, Pseudomonas taetrolens, Pseudomonas mohnii, Pseudomonas moorei, Pseudomonas moraviensis, Pseudomonas gessardii, Pseudomonas cichorii, Pseudomonas libanensis, Pseudomonas benzenivorans, Pseudomonas panacis, Pseudomonas umsongensis, Pseudomonas reinekei, Pseudomonas fluorescens, Pseudomonas agarici, Pseudomonas lutea, Pseudomonas mucidolens, Pseudomonas azotoformans, Pseudomonas viridiflava, Pseudomonas koreensis, Pseudomonas kuykendallii, Pseudomonas synxantha, Pseudomonas segetis, Pseudomonas marincola, Pseudomonas cedrina* subsp. *cedrina, Pseudomonas graminis, Pseudomonas vancouverensis, Pseudomonas cedrina* subsp. *fulgida, Pseudomonas plecoglossicida, Pseudomonas cuatrocienegasensis, Pseudomonas taiwanensis, Pseudomonas putida, Pseudomonas rhizosphaerae, Pseudomonas anguilliseptica, Pseudomonas monteilii, Pseudomonas fuscovaginae, Pseudomonas mosselii, Pseudomonas taeanensis, Pseudomonas asplenii, Pseudomonas entomophila, Pseudomonas cremoricolorata, Pseudomonas parafulva, Pseudomonas alcaliphila, Pseudomonas oleovorans* subsp. *lubricantis, Pseudomonas borbori, Pseudomonas composti, Pseudomonas toyotomiensis, Pseudomonas batumici, Pseudomonas flavescens, Pseudomonas vranovensis, Pseudomonas punonensis, Pseudomonas balearica, Pseudomonas indoloxydans, Pseudomonas guineae, Pseudomonas japonica, Pseudomonas stutzeri, Pseudomonas seleniipraecipitans, Pseudomonas peli, Pseudomonas fulva, Pseudomonas argentinensis, Pseudomonas xanthomarina, Pseudomonas pohangensis, Pseudomonas oleovorans, Pseudomonas mendocina, Pseudomonas luteola, Pseudomonas straminea, Pseudomonas caeni, Pseudomonas aeruginosa, Pseudomonas tuomuerensis, Pseudomonas azotifigens, Pseudomonas indica, Pseudomonas oryzihabitans Pseudomonas otitidis,*

*Pseudomonas psychrotolerans, Pseudomonas zeshuii, Pseudomonas resinovorans, Pseudomonas oleovorans* subsp. *oleovorans, Pseudomonas thermotolerans, Pseudomonas bauzanensis, Pseudomonas duriflava, Pseudomonas pachastrellae, Pseudomonas citronellolis, Pseudomonas alcaligenes, Pseudomonas xinjiangensis, Pseudomonas delhiensis, Pseudomonas sabulinigri, Pseudomonas litoralis, Pseudomonas pelagia, Pseudomonas linyingensis, Pseudomonas knackmussii, Pseudomonas panipatensis, Pseudomonas nitroreducens, Pseudomonas nitritireducens, Pseudomonas jinjuensis, Pseudomonas pertucinogena, Pseudomonas xiamenensis, Pseudomonas cissicola, Pseudomonas halophile, Pseudomonas boreopolis, Pseudomonas geniculate, Pseudomonas beteli, Pseudomonas hibiscicola, Pseudomonas pictorum, Pseudomonas carboxydohydrogena*. The *Pseudomonas* species may also have the following identifying characteristics:

(i) enzymatic activity for acid and alkaline phosphatase, leucine arylamidase and naphthol-A5-BI-phosphohydrolase;

(ii) is resistant to tetracycline, erythromycin, streptomycin, penicillin, ampicillin, chromamphenicol and cefuroxome (iii) a 16S rRNA gene sequence comprising a forward sequence set forth in SEQ ID NO:3, a reverse sequence set forth in SEQ ID NO:4 and a consensus sequence set forth in SEQ ID NO:5

(iv) contains the fatty acids 17:0, 3OH, 16:0, 1:0, 3OH (v) produces pyoluteorin and 2,4-diacetylphologlucinol.

The compounds may have the following molecular weights and HPLC retention times:

(i) a molecular weight of: about 300-380 and more particularly, about 324 as determined by Liquid Chromatography/Mass Spectroscopy (LC/MS) and an HPLC retention time of about 12-22 minutes, more specifically about 17 minutes and even more specifically about 17.50 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm; and has a UV absorption at 212, 252, 312 nm;

(ii) a molecular weight of about 300-360 and more particularly, about 314 as determined by LC/MS; and an HPLC retention time of about 10-20 minutes, more specifically about 15 minutes and even more specifically about 15.23 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and has a UV absorption at 299, 311, 325 nm;

(iii) a molecular weight of about 580-680 and more particularly, about 627 as determined by LC/MS and an HPLC retention time of 8-20 minutes, more specifically about 14 minutes and even more specifically about 14.24 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and has a UV absorption at 299, 311, 325 nm;

(iv) a molecular weight of about 350-425 and more particularly, about 386 as determined by LC/MS and an HPLC retention time of about 6-16 minutes, more specifically about 9 minutes and even more specifically about 9.06 min on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm; and has a UV absorption at 221, 267, 361 nm.

Furthermore, the substances may be compounds such as peptides, proteins and/or lactones. Examples of such substances are disclosed in US Patent Application Pub. No. 20100266717, the contents of which are incorporated herein by reference and include but are not limited to:

(I) a compound that (a) has a molecular weight of about 1280-1310 as determined by Liquid Chromatography/Mass Spectroscopy (LC/MS); (b) has 1H NMR values of δ 9.25, 8.36, 8.06, 7.82, 7.71, 7.52, 7.45, 6.82, 6.36, 6.08, 5.42, 5.39, 5.30, 5.14, 4.68, 4.42, 4.31, 4.16, 4.11, 4.07, 3.95-3.86, 3.83, 3.72, 3.66, 3.53, 3.48, 3.37, 3.17, 3.06, 2.56, 2.53, 2.45, 2.32, 2.21, 2.02, 1.96, 1.84, 1.72, 1.65, 1.61, 1.51, 1.48-1.37, 1.32, 1.12, 0.94, 0.91, 0.68; (c) has an (High Pressure Liquid Chromatography) (HPLC) retention time of about 50-55 min on a reversed phase C-18 HPLC column using a water:acetonitrile gradient solvent system (0-10 min; 30-40% aqueous $CH_3CN$, 10-20 min; 40-60% aqueous $CH_3CN$, 20-60 min; 60-80% aqueous $CH_3CN$, 60-65 min; 80-100% aqueous $CH_3CN$) at 2.5 mL/min flow rate and UV detection of 210 nm;

(II) a compound that has (a) a molecular weight of about 1310-1335, more particularly, about 1321 as determined by LC/MS; (b) has an HPLC retention time of about 55-60 min on a reversed phase C-18 HPLC column using a water:acetonitrile gradient solvent system (0-10 min; 30-40% aqueous $CH_3CN$, 10-20 min; 40-60% aqueous $CH_3CN$, 20-60 min; 60-80% aqueous $CH_3CN$, 60-65 min; 80-100% aqueous $CH_3CN$) at 2.5 mL/min flow rate and UV detection of 210 nm;

(III) a compound that (a) has a molecular weight of about 540-550 as determined by LC/MS; (b) has an HPLC retention time of about 50-55 min on a reversed phase C-18 HPLC column using a water:acetonitrile solvent system (0-10 min; 35-45% aqueous $CH_3CN$, 10-20 min; 45-60% aqueous $CH_3CN$, 20-50 min; 60-85% aqueous $CH_3CN$, 50-60 min; 85-100% aqueous $CH_3CN$, 60-70 min; 100% $CH_3CN$) at 10 mL/min flow rate and UV detection of 210 nm.

In a particular embodiment, the compound may be derived from *Pseudomonas fluorescens* or *Pseudomonas protegens* and particularly from *Pseudomonas* strain having the identifying characteristics of ATCC 55799 and has a hydroxylated unsaturated fatty acid lactone structure comprising at least one lactone moiety which is a 5 membered γ-lactone, at least one unsaturated moiety and at least one alcohol group; a molecular weight from 285 to about 310 in the core structure; at least 15 carbons and at least 3 oxygen atoms. In a more particular embodiment, the compound may have the structure

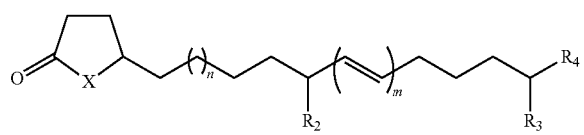

wherein: X are each independently —O, —NR$_1$, or —S, wherein R$_1$ is —H or C$_1$-C$_6$ alkyl; n=0 to 15, R$_2$ to R$_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond or triple bond. In yet another particular embodiment, Y and M are oxygen, A and X are carbon and n is 2 or 3, R is a C7 or C8 alkyl and z is 0, wherein when n is 2 and R is a C7 alkyl, R is attached to A.

In a particular embodiment, the compound is piliferolide A

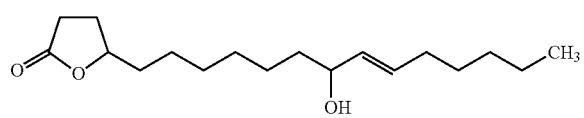 [SMILES: CCCCC/C=C/C(O)CCCCCCC1CCC(=O)O1]

In yet another particular embodiment, the compound may be derived from *Pseudomonas fluorescens* or *protegens* strain and is characterized as having a hydroxylated unsaturated fatty acid structure comprising at least one carboxylic acid moiety, at least one unsaturated moiety and at least one alcohol group; molecular weight from 285 to about 310 in the core structure; at least 15 carbons and at least 3 oxygens.

In a more particular embodiment, there are provided compounds having the structure

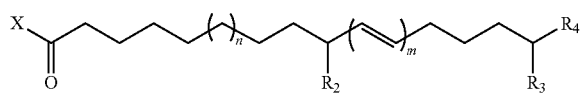

wherein: X are each independently —OH, —NR$_1$, or —S, wherein R$_1$ is —H or C$_1$-C$_6$ alkyl; n=0 to 15, R$_2$ to R$_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond, triple bond, with a molecular weight of between about 285 to about 310.

In a most specific embodiment, the compound is 11-hydroxy-12-ene-octadecanoic acid and has the structure

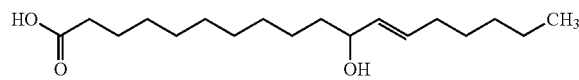 [SMILES: CCCCC/C=C/C(O)CCCCCCCCCC(=O)O]

Other compounds disclosed in US Patent Application Pub. No. 20100266717 include but are not limited to:

(a) a lactone selected from the group consisting of gamma-dodecalactone, delta-tridecalactone, piliferolide A and alpha-heptyl-gamma-butyrolactone and (b) a sarmentine analog selected from the group consisting of N-Cyclopentyldecanamide, N-(Decanoyl)pyrrolidine, N-(Decanoyl)piperidine, N-(Decanoyl)hexamethyleneimine, N-Cyclopentyldecanamide, (N-(Decenoyl)pyrrolidine, N-(Decenoyl)piperidine, N-(Decenoyl)hexamethyleneimine and N-(Decenoyl)piperidine and (c) 11-hydroxy-12-ene-octadecanoic acid.

In addition to the compounds disclosed in US Patent Application Pub. No. 20100266717, the substance may be a compound that (a) has molluscidal activity; (b) has a molecular weight of about 230-270 as determined by Liquid Chromatography/Mass Spectroscopy (LC/MS) and (c) has an High Pressure Liquid Chromatography (HPLC) retention time of about 16-25 minutes on a reversed phase C-18 HPLC column using a water:acetonitrile (CH$_3$CN) gradient solvent system (0-20 min; 90-0% aqueous CH$_3$CN, 20-24 min; 100% CH$_3$CN, 24-27 min; 0-90% aqueous CH$_3$CN, 27-30 min; 90% aqueous CH$_3$CN) at 0.5 mL/min flow rate and UV detection of 210 nm and, the compound in one embodiment may be a unsaturated fatty acid.

In a more particular embodiment, there are provided compounds including but not limited to:

(A) a compound having the structure

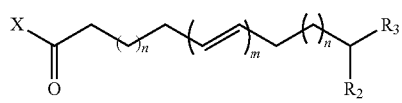

or an acceptable salt or steriosomers thereof, wherein: X are each independently —OH, —NR$_1$, or —S, wherein R$_1$ is —H or C$_1$-C$_6$ alkyl; n=0 to 15, R$_2$, R$_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond, triple bond.

(B) a compound having the structure

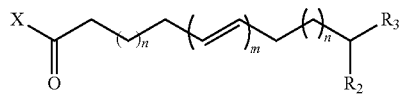

or an acceptable salt or steriosomers thereof, wherein: X are each independently —OH, —NR$_1$, or —S, wherein R$_1$ is —H or C$_1$-C$_6$ alkyl; n=0 to 15, R$_2$, R$_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=0 to 15, In a most specific embodiment, the compound is 9-hexadecenoic acid

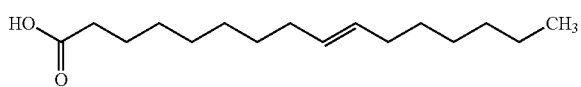 [SMILES: CCCCCC/C=C/CCCCCCCC(=O)O]

In a particular embodiment, the compound may be derived from *Pseudomonas fluorescens* or *protegens* and characterized as having a hydroxylated unsaturated fatty acid structure comprising at least one carboxylic acid moiety, at least one unsaturated moiety and at least one alcohol group; molecular weight from 280 to about 320 in the core structure; at least 15 carbons and at least 3 oxygens.

In a more particular embodiment, there are provided compounds including but not limited to:

(A) a compound having the structure

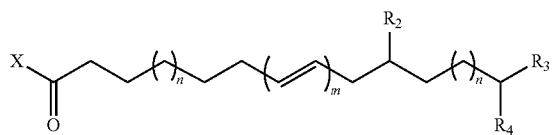

or a acceptable salt or stereoisomers thereof, wherein: X are each independently —OH, —NR$_1$, or —S, wherein R$_1$ is —H or C$_1$-C$_6$ alkyl; n=0 to 15, R$_2$ to R$_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond, triple bond.

(B) a compound having the structure

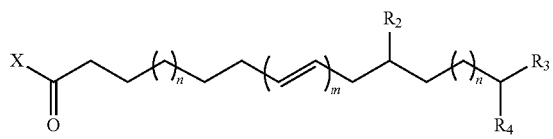

wherein R$_1$ is —H or C$_1$-C$_6$ alkyl; n=0 to 15, R$_2$ to R$_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=0 to 15.

In a particular embodiment, the compound is ricinoleic acid

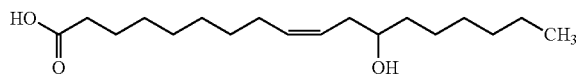 [SMILES: CCCCCCC(O)C/C=C\CCCCCCCC(=O)O]

Methods of Production

As noted above, the compounds and compositions may be obtained, is obtainable or derived from an organism having the identifying characteristics of a *Pseudomonas* species, or strain set forth above. The methods comprise cultivating these organisms and optionally obtaining the compounds by isolating these compounds from the cells of these organisms.

In particular, the organisms are cultivated in a nutrient medium using methods known in the art. The organisms may be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation may take place in suitable nutrient medium comprising carbon and nitrogen sources and inorganic salts, using procedures known in the art. Suitable media are available may be available from commercial sources or prepared according to published compositions. A particular embodiment is disclosed in the examples infra and in U.S. Pat. No. 6,194,194.

After cultivation, the cells may be concentrated and subsequently suspended in a buffer to obtain a cell suspension. In one embodiment, a suspension of dead cells is used. Live cells in the cellular suspension may be killed by at least one of the following: irradiating, heating, drying, or treating cells with other chemical of physical means. A dead cell suspension is not required for activity against mussel species.

In a particular embodiment, substances which modulate and in particular are toxic to phytopathogenic microorganisms may be extracted from the suspension. The extract may be fractionated by chromatography. Chromatographic fractions may be assayed for toxic activity against bacteria, such as *Xanthomonas campestris, Xanthomomnas vesicatoria, Bacillus cereus, Bacillus subtilis*, using methods known in the art; one particular embodiment is disclosed in the examples, infra. This process may be repeated one or more times using the same or different chromatographic methods.

Compositions

Compositions may comprise whole cell broth cultures, liquid cultures, or suspensions of a strain from *Pseudomonas* sp., e.g. a strain having the identifying characteristics of *Pseudomonas* sp. that may be selected from the group consisting of *Pseudomonas protegens, Pseudomonas saponiphila, Pseudomonas ficuserectae, Pseudomonas congelans, Pseudomonas tremae, Pseudomonas caricapapayae, Pseudomonas mandelii, Pseudomonas savastanoi, Pseudomonas syringae, Pseudomonas chlororaphis* subsp. *piscium, Pseudomonas cannabina, Pseudomonas marginalis, Pseudomonas simiae, Pseudomonas avellanae, Pseudomonas chlororaphis* subsp. *aurantiaca, Pseudomonas chlororaphis* subsp. *chlororaphis, Pseudomonas frederiksbergensis, Pseudomonas amygdali, Pseudomonas extremaustralis, Pseudomonas kilonensis, Pseudomonas lini, Pseudomonas Antarctica, Pseudomonas corrugata, Pseudomonas poae, Pseudomonas grimontii, Pseudomonas brassicacearum* subsp. *Neoaurantiaca, Pseudomonas meridian, Pseudomonas trivialis, Pseudomonas veronii, Pseudomonas lundensis, Pseudomonas salomonii, Pseudomonas rhodesiae, Pseudomonas arsenicoxydans, Pseudomonas thivervalensis, Pseudomonas deceptionensis, Pseudomonas palleroniana, Pseudomonas chlororaphis* subsp. *aureofaciens, Pseudomonas costantinii, Pseudomonas lurida, Pseudomonas migulae, Pseudomonas orientalis, Pseudomonas extremorientalis, Pseudomonas mediterranea, Pseudomonas brassicacearum* subsp. *brassicacearum, Pseudomonas abietaniphila, Pseudomonas baetica, Pseudomonas brenneri, Pseudomonas psychrophila, Pseudomonas jessenii, Pseudomonas fragi, Pseudomonas tolaasii, Pseudomonas proteolytica, Pseudomonas taetrolens, Pseudomonas mohnii, Pseudomonas moorei,*

*Pseudomonas moraviensis, Pseudomonas gessardii, Pseudomonas cichorii, Pseudomonas libanensis, Pseudomonas benzenivorans, Pseudomonas panacis, Pseudomonas umsongensis, Pseudomonas reinekei, Pseudomonas fluorescens, Pseudomonas agarici, Pseudomonas lutea, Pseudomonas mucidolens, Pseudomonas azotoformans, Pseudomonas viridiflava, Pseudomonas koreensis, Pseudomonas kuykendallii, Pseudomonas synxantha, Pseudomonas segetis, Pseudomonas marincola, Pseudomonas cedrina* subsp. *cedrina, Pseudomonas graminis, Pseudomonas vancouverensis, Pseudomonas cedrina* subsp. *fulgida, Pseudomonas plecoglossicida, Pseudomonas cuatrocienegasensis, Pseudomonas taiwanensis, Pseudomonas putida Pseudomonas rhizosphaerae, Pseudomonas anguilliseptica, Pseudomonas monteilii, Pseudomonas fuscovaginae, Pseudomonas mosselii, Pseudomonas taeanensis, Pseudomonas asplenii, Pseudomonas entomophila, Pseudomonas cremoricolorata, Pseudomonas parafulva, Pseudomonas alcaliphila, Pseudomonas oleovorans* subsp. *lubricantis, Pseudomonas borbori, Pseudomonas composti, Pseudomonas toyotomiensis, Pseudomonas batumici, Pseudomonas flavescens, Pseudomonas vranovensis, Pseudomonas punonensis, Pseudomonas balearica, Pseudomonas indoloxydans, Pseudomonas guineae, Pseudomonas japonica Pseudomonas stutzeri, Pseudomonas seleniipraecipitans, Pseudomonas peli, Pseudomonas fulva, Pseudomonas argentinensis, Pseudomonas xanthomarina, Pseudomonas pohangensis, Pseudomonas oleovorans, Pseudomonas mendocina, Pseudomonas luteola, Pseudomonas straminea, Pseudomonas caeni, Pseudomonas aeruginosa, Pseudomonas tuomuerensis, Pseudomonas azotifigens, Pseudomonas indica, Pseudomonas oryzihabitans, Pseudomonas otitidis, Pseudomonas psychrotolerans, Pseudomonas zeshuii, Pseudomonas resinovorans, Pseudomonas oleovorans* subsp. *oleovorans, Pseudomonas thermotolerans, Pseudomonas bauzanensis, Pseudomonas duriflava, Pseudomonas pachastrellae, Pseudomonas citronellolis, Pseudomonas alcaligenes, Pseudomonas xinjiangensis, Pseudomonas delhiensis, Pseudomonas sabulinigri, Pseudomonas litoralis, Pseudomonas pelagia, Pseudomonas linyingensis, Pseudomonas knackmussii, Pseudomonas panipatensis, Pseudomonas nitroreducens, Pseudomonas nitritireducens, Pseudomonas jinjuensis, Pseudomonas pertucinogena, Pseudomonas xiamenensis, Pseudomonas cissicola, Pseudomonas halophile, Pseudomonas boreopolis, Pseudomonas geniculate, Pseudomonas beteli, Pseudomonas hibiscicola, Pseudomonas pictorum, Pseudomonas carboxydohydrogena*. In a specific embodiment, the *Pseudomonas* species is *Pseudomonas protogens* or *Pseudomonas fluorescens* and more particularly, having the identifying characteristics of ATCC (see U.S. Pat. No. 6,194,194), as well as supernatants, filtrates, fractions, extracts or compounds, including metabolites, derived from a strain of a *Pseudomonas* sp set forth above or combinations of the foregoing which in particular have antibacterial activity.

The compositions set forth above can be formulated in any manner. Non-limiting formulation examples include, but are not limited to, Emulsifiable concentrates (EC), Wettable powders (WP), soluble liquids (SL), Aerosols, Ultra-low volume concentrate solutions (ULV), Soluble powders (SP), Microencapsulation, Water dispersed Granules, Flowables (FL), Microemulsions (ME), Nano-emulsions (NE), etc. In any formulation described herein, percent of the active ingredient is within a range of 0.01% to 99.99%.

The compositions may be in the form of a liquid, gel or solid. A solid composition can be prepared by suspending a solid carrier in a solution of active ingredient(s) and drying the suspension under mild conditions, such as evaporation at room temperature or vacuum evaporation at 65° C. or lower. A composition may comprise gel-encapsulated active ingredient(s). Such gel-encapsulated materials can be prepared by mixing a gel-forming agent (e.g., gelatin, cellulose, or lignin) with a culture or suspension of live or inactivated *Pseudomonas* or a cell-free filtrate or cell fraction of a *Pseudomonas* culture or suspension, or a spray- or freeze-dried culture, cell, or cell fraction or in a solution of antibacterial compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The compositions may also include but are not limited to aminoglycoside antibiotics which include a number of molecules (e.g. kanamycin, neomycin, gentamycin, derivative G418 and paromycin) which are toxic to plant, fungal and animal cells (Nap et al. 1992) as well as bacterial neomycin phosphotransferase II and aerocyanidin, aerocavin, 3,6-dihydroxy-indoxazene, and monobactam SB-26.180.

Uses

As noted above, the compositions and substances set forth above may be used to modulate the amount of phytopathogenic microorganism infestation in plants, their seeds, roots, fruits, foliage, stems, tubers, and in particular, prevent or inhibit and/or prevent said phytopathogenic microorganism infection, in particular, soil-borne disease and/or decrease the rate and/or degree of spread of said soil borne disease infection in said plants. Again, the plants include but are not limited to fruits (e.g., strawberry, blueberry, blackberry, peach and other stone fruits), vegetable (e.g., tomato, squash, pepper, eggplant, potatoes, carrots), or grain crops (e.g., soy, wheat, rice, corn, sorghum), trees, flowers, ornamental plants, shrubs (e.g., cotton, roses), bulb plants (e.g., onion, garlic) or vines (e.g., grape vine), turf, tubers (e.g. potato, carrots, beets). Alternatively, said compositions may be used to modulate the amount of soil-borne disease infection in plants and in particular, prevent or inhibit said soil borne disease infection and/or decrease the rate and/or degree of spread of said soil borne disease infection in said plants. Again, the plants include but are not limited to (e.g., strawberry), vegetable (e.g., tomato, squash, pepper, eggplant), or grain crops (e.g., soy, wheat, rice, corn), trees, flowers, ornamental plants, shrubs (e.g., cotton, roses), bulb plants (e.g., onion, garlic) or vines (e.g., grape vine). Soil borne diseases include, but are not limited to, those caused by infection by soil borne microorganisms such as *Xanthomonas campestris, Xanthomomnas vesicatoria, Bacillus cereus, Botrytis cinerea* and *Bacillus subtilis, Erwinia, S. fulginea.*

Application of an effective antimicrobial (e.g. antibacterial, antifungal) control amount of a supernatant, filtrate or extract containing a antimicrobially (e.g. antibacterially, antifungally) active metabolite, or compound produced by or obtained or derived from a supernatant, filtrate or extract of *Pseudomonas* sp. or application of combinations of the foregoing is provided. The strain or supernatant or filtrate or extract, metabolite and/or compound are applied, alone or in combination with another pesticidal substance, in an effective pest control or pesticidal amount. An effective amount is defined as those quantities of microorganism cells, supernatant, filtrate or extract, metabolite and/or compound alone or in combination with another pesticidal substance that is sufficient to modulate pest infestation. The effective rate can be affected by pest species present, stage of pest growth, pest population density, and environmental factors such as temperature, wind velocity, rain, time of day and seasonality. The amount that will be within an effective range in a particular instance can be determined by laboratory or field tests.

EXAMPLES

The composition and methods set forth herein will be further illustrated in the following, non-limiting Examples. The examples are illustrative of various embodiments only and do not limit the claimed invention regarding the materials, conditions, weight ratios, process parameters and the like recited herein.

Example 1: Analysis of *Pseudomonas* Strain CL145A (ATCC 55799)

The *Pseudomonas* strain CL145A (ATCC 55799) has been further characterized through a polyphasic approach by investigating its phenotypic and genotypic characteristics. The results from the studies disclosed herein indicate that CL145A is a better match to *Pseudomonas protegens*, rather than *Pseudomonas fluorescens*.

Recent developments in the taxonomical study of the genus *Pseudomonas* resulted in the creation of a new species *Pseudomonas protegens*, *Pseudomonas protegens* includes several strains formerly identified as *Pseudomonas fluorescens* including strains CHA0, PF, PGNL1, PGNR 1, PGNR 2, PGNR 3, PGNR 4, PINR 3 and Pf1. The basis of the reclassification is described by Ramette et al., (2011), and was officially validated in 2012 (Euzeby, 2012). Based on this new information, the best match for CL145A is *Pseudomonas protegens*. MBI-401 will now be identified as *Pseudomonas protegens* strain CL145A (CL145A).

CL145A was characterized through a polyphasic approach investigating phenotypic and genotypic characteristics, as well as confirmation of the presence of two metabolites; 2,4-Diacetylphloroglucinol and Pyoluteorin. Pyoluteorin and 2,4-Diacetylphloroglucinol (see FIG. 3) are central characteristics to the differentiation of *Pseudomonas fluorescens* and *Pseudomonas protegens*. Isolates that do not produce these two compounds, or that only produce one of them, remain known as *Pseudomonas fluorescens*, while *Pseudomonas fluorescens* that produce both compounds have been reclassified as *Pseudomonas protegens* as described by Ramette et al., (2011).

1.1 Analysis of Biochemical, Physiological and Metabolic Characteristics

*Pseudomonas protegens* strain CL145A (ATCC 55799) was subjected to biochemical testing to characterize the isolate and create a baseline for further tracking. As part of this characterization strategy, the growth of CL145A was tested at temperatures of 16° C. and 37° C., and API ZYM and API 20NE assays were performed, which allowed for semiquantitation of enzymatic activities (API ZYM) and identification of Gram-negative non-Enterobacteriaceae (API 20NE). Fatty Acid Profiles and MALDI-TOF profiles were performed as well.

1.1.1 Growth at 16° C. and 37° C.

*Pseudomonas* species are known to grow at a wide range of temperatures, with 28° C. reported as the optimal for many species, and ranging from 4° C. to 45° C. for some species. *Pseudomonas fluorescens* does not grow at 41° C., but some strains show growth as low as 4° C. (Palleroni, 2005).

A dilute cell suspension of CL145A was prepared in phosphate buffer. The suspension was inoculated onto agar plates and incubated overnight at 16° C. and 37° C. Incubators were set at the proper temperatures and allowed to equilibrate overnight before incubations took place. CL145A grew well at both temperatures.

1.1.2. API ZYM

API ZYM provides a platform for rapid semi-quantitation of enzymatic activity. The assay was performed at MBI's facilities, following the manufacturer's directions (Biomerieux). A 1 day PDA plate was inoculated from a glycerol stock of CL145A (ATCC 55799), and incubated overnight at 25° C. Colonies growing on the plate were used to inoculate the API ZYM strip according to manufacturer's instructions, and incubated at 30° C. for 48.5 hours. Results are shown in Table 1 below.

TABLE 1

API ZYM test results for CL145A (ATCC 55799)

| No | Enzyme assayed for | Substrate | pH | Positive | Negative | Rating | Result |
|---|---|---|---|---|---|---|---|
| 1 | Control | | 8.5 | | Colorless or color of the sample if it has intense coloration | 0 | − |
| 2 | Alkaline phosphatase | 2-naphthyl phosphate | 6.5 | Violet | Colorless or very pale yellow | 5 | + |
| 3 | Esterase (C 4) | 2-naphythyl butyrate | 7.5 | Violet | | 0 | − |
| 4 | Esterase Lipase (C 8) | 2-naphthyl caprylate | 7.5 | Violet | | 0 | − |
| 5 | Lipase (C 14) | 2-naphthyl myristate | 7.5 | Violet | | 0 | − |
| 6 | Leucinearylamidase | L-leucyl-2-naphthylamide | 7.5 | Orange | | 4 | + |
| 7 | Valinearylamidase | L-valyl-2-naphthylamide | 7.5 | Orange | | 0 | − |
| 8 | Cysteine arylamidase | L-cystyl-2-naphthylamide | 7.5 | Orange | | 0 | − |

TABLE 1-continued

API ZYM test results for CL145A (ATCC 55799)

| No | Enzyme assayed for | Substrate | pH | Positive | Negative | Rating | Result |
|---|---|---|---|---|---|---|---|
| 9 | Trypsin | N-benzoyl-DL-arginine-2-naphthylamide | 8.5 | Orange | | 0 | − |
| 10 | α-chymotrypsin | N-glutaryl-phenylalanine-2-naphthylamide | 7.5 | Orange | | 0 | − |
| 11 | Acid phosphatase | 2-naphthyl phosphate | 5.4 | Violet | | 5 | + |
| 12 | Naphthol-AS-BI-phosphohydrolase | Naphthol-AS-BI-phosphate | 5.4 | Blue | | 5 | + |
| 13 | α-galactosidase | 6-Br-2-naphthyl-αD-galactopyranoside | 5.4 | Violet | | 0 | − |
| 14 | β-galactosidase | 2-naphthyl-βD-galactopyranoside | 5.4 | Violet | | 0 | − |
| 15 | β-glucuronidase | Naphthol-AS-BI-βD-glucuronide | 5.4 | Blue | | 0 | − |
| 16 | α-glucosidase | 2-naphthyl-αD-glucopyranoside | 5.4 | Violet | | 0 | − |
| 17 | β-glucosidase | 6-Br-2-naphthyl-βD-glucopyranoside | 5.4 | Violet | | 0 | − |
| 18 | N-acetyl-β-glucosaminidase | 1-naphthyl-N-acetyl-βD-glucosaminide | 5.4 | Brown | | 0 | − |
| 19 | α-mannosidase | 6-Br-2-naphthyl-αD-mannopyranoside | 5.4 | Violet | | 0 | − |
| 20 | α-fucosidase | 2-naphthyl-αL-fucopyranoside | 5.4 | Violet | | 0 | − |

The results indicated that CL145A (ATCC 55799) has strong enzymatic activity for acid and alkaline phosphatase, leucine arylamidase and naphthol-AS-BI-phosphohydrolase. Negative results were recorded for all other enzyme tests.

1.1.3. API 20NE

API 20NE allows for semiquantitation of enzymatic activities and identification of Gram-negative non-Enterobacteriaceae. The assay was performed following manufacturer's directions (Biomerieux). A 1 day PDA plate was inoculated from a glycerol stock of CL145A (ATCC 55799), and incubated overnight at 25° C. Colonies growing on the plate were used to inoculate the API 20NE strip according to manufacturer's instructions, and incubated at 30° C. for 48.5 hours. Results are shown in Table 2.

TABLE 2

API 20NE test results for CL145A (ATCC 55799)

| Test | Active Ingredient | Reaction/Enzymes | Negative (Results) | Positive (Results) | Summary |
|---|---|---|---|---|---|
| NO₃ | Potassium Nitrate | Reduction of nitrates to nitrites | Colorless | Pink-Red | − |
| | | Reduction of nitrates to nitrogen | Pink | Colorless | NA |
| TRP | L-tryptophane | Indole production (tryptophan) | Colorless | Pink | − |
| GLU | D-glucose | Fermentation (glucose) | Pale-green/yellow Blue to green | Yellow | − |
| ADH | L-arginine | Arginine Dihydrolase | Yellow | Orange/pink/red | + |
| URE | Urea | Urease | Yellow | Orange/pink/red | + |
| ESC | Esculin ferric citrate | Hydrolysis (β-glucosidase)(esculin) | Yellow | Grey/brown/black | − |
| GEL | Gelatin (bovine origin) | Hydrolysis (protease) (gelatin) | No pigment diffusion | Diffusion of black pigment | + |
| PNPG | 4-nitrophenyl-βD-galactopyranoside | B-galactosidase (Para-nitrophenyl-βD-galactopyranosidase) | Colorless | Yellow | − |
| |GLU| | D-glucose | Assimilation of glucose | Transparent | Opaque | + |
| |ARA| | L-arabinose | Assimilation of arabinose | Transparent | Opaque | ± |
| |MNE| | D-mannose | Assimilation of mannose | Transparent | Opaque | + |
| |MAN| | D-mannitol | Assimilation of mannitol | Transparent | Opaque | + |
| |NAG| | N-acetyl-glucosamine | Assimilation of n-acetyl-glucosamine | Transparent | Opaque | + |
| |MAL| | D-maltose | Assimilation of maltose | Transparent | Opaque | − |
| |GNT| | Potassium gluconate | Assimilation of potassium gluconate | Transparent | Opaque | + |
| |CAP| | Capric acid | Assimilation of capric acid | Transparent | Opaque | + |

TABLE 2-continued

API 20NE test results for CL145A (ATCC 55799)

| Test | Active Ingredient | Reaction/Enzymes | Results Negative | Positive | Summary |
|---|---|---|---|---|---|
| |ADI| | Adipic acid | Assimilation of adipic acid | Transparent | Opaque | + |
| |MLT| | Malic acid | Assimilation of malate | Transparent | Opaque | + |
| |CIT| | Trisodium citrate | Assimilation of trisodium citrate | Transparent | Opaque | + |
| |PAC| | Phenylacetic acid | Assimilation of phenylacetic acid | Transparent | Opaque | + |

Key:
+ (Positive),
− (Negative),
± (weak)

*Pseudomonas protegens* does not reduce nitrate. Additionally, Ramette et al. (2011) report that *P. protegens* can assimilate N-acetyl-D-glucosamine, while *P. fluorescens* cannot. CL145A can assimilate N-acetyl-D-glucosamine according to API 20 NE results. CL145A and *P. protegens* also share the ability to assimilate phenyl acetate (*P. fluorescens* cannot). CL145A displayed negative glucuronidase activity in the API ZYM test. *P. protegens* cannot assimilate D-glucuronate, while *P. fluorescens* can assimilate D-glucuronate.

In summary, CL145A (also referred to as ATCC 55799 or MBI-401) shares many phenotypic traits that differentiate it from *P. fluorescens* and indicate closer similarity to *P. protegens*. However, *Pseudomonas* identification based on phenotypic characteristics can be difficult and an ultimate identification always requires a DNA-based approach.

1.1.4. Antibiotic Resistance Profile

One glycerol stock vial of CL145A was equally distributed onto Mueller-Hinton Agar plates (100 μl per plate) and spread on the plate using a sterile cell spreader. Antibiotic discs were then placed onto the plates along with a blank sterile disc. Plates were incubated at 25° C. in the dark for 72 hours. Results are shown in Table 3.

TABLE 3

Antibiotic resistance profile for CL145A (ATCC 55799)

| Antibiotic tested | Concentration (μg) | Suppresses growth of CL145A |
|---|---|---|
| Tetracycline | 30 | No |
| Kanamycin | 30 | Yes |
| Erythromycin | 15 | No |
| Streptomycin | 10 | No |
| Penicillin | 10 | No |
| Ampicillin | 10 | No |
| Oxytetracycline | 30 | Yes |
| Chloramphenicol | 30 | No |
| Ciprofloxacin | 5 | Yes |
| Gentamicin | 10 | Yes |
| Piperacillin | 100 | Yes |
| Cefuroxime | 30 | No |
| Imipenem | 10 | Yes |
| Sulphamethoxazole-Trimethoprim | 23.75/25 | Yes |

Figure 3:
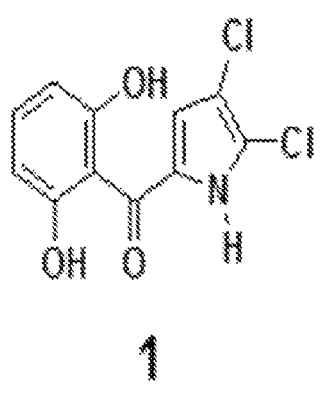
FIG. 3 shows the structure for pyoluteorin (1) and DAPG (2).
Figure 3:
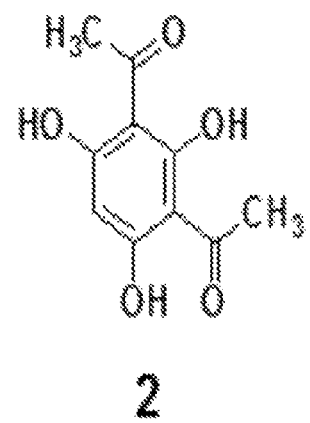

The antibiotic profile results indicated that CL145A is resistant to tetracycline, erythromycin, streptomycin, penicillin, ampicillin, chloramphenicol and cefuroxime as shown in FIG. 3 as growth of CL145A was not inhibited by the antibiotic disc; and shown to be sensitive to kanamycin, oxytetracycline, ciprofloxacin, gentamicin, piperacillin, imipenem and sulphamethoxazole-treimethoprim as growth of CL145A was inhibited following 72 hours incubation.

1.1.5. Analysis of Fatty Acid Methyl Ester Composition (FAME Analysis)

An agar plate with 24-hour old colonies of CL145A was submitted for Fatty Acid Methyl Ester (FAME) profiling to Microbial ID, Inc. (Newark, N.J.). The main fatty acids found are described below in Table 4.

TABLE 4

FAME analysis for CL145A (ATCC 55799)

| Lipid name | % of total |
|---|---|
| Sum In Feature 2 | 0.45 |
| 10:0 | 0.36 |
| 10:0 3OH | 4.74 |
| 14:0 | 0.46 |
| 12:0 | 1.91 |
| Sum In Feature 3 | 32.23 |
| 16:0 | 26.89 |
| 12:0 2OH | 5.15 |
| 12:1 3OH | 1.01 |
| 12:0 3OH | 5.54 |
| 16:1 w5c | 0.11 |
| 17:0 iso | 0.10 |
| 16:0 3OH | 4.41 |
| Sum In Feature 8 | 18.69 |
| 18:0 | 0.65 |
| 18:1 w7c 11-methyl | 0.18 |
| 17:0 | 0.10 |
| 17:0 cyclo | 1.42 |

The FAME profile for CL145A appears to match with a *Pseudomonas putida* biotype A strain in the database, showing the highest similarity index (0.730). The next three best matches were with *Pseudomonas fluorescens* biotype A, biotype B and biotype G, all with similarity indices below 0.700.

1.2. 16S rRNA Gene Amplification and Sequencing 1.2.1 DNA Extraction of CL145A (ATCC 55799)

*Pseudomonas protegens* strain CL145A (ATCC 55799) was streaked on fresh potato dextrose plates and allowed to grow for 2-3 days or until enough biomass was evident. A loopful of the bacterium was suspended in DNA extraction buffer (included in the MoBio Ultra Clean Microbial DNA Extraction Kit, Cat No. 12224-50, Carlsbad, Calif., USA) using a sterile loop. DNA was extracted using the MoBio Ultra Clean Microbial DNA extraction kit using the manufacturer's protocol. DNA extract was checked for quality and quantity by running a 5 μL aliquot on a 1% agarose gel.

1.2.2 PCR Amplification of the 16S rRNA Gene from CL145A (ATCC 55799)

PCR reactions for the amplification of the 16s rRNA gene were performed by combining 1.5 ul of DNA extract CL145A (ATCC 55799) with 20 μL nuclease-free sterile water, 25 μL GoTaq Green Mastermix (Promega), μL forward primer (SEQ ID NO:1), and 1.5 μL reverse primer (SEQ ID NO:2). The PCR reaction was performed using a thermocycler PCR machine under the following conditions: 10 minutes at 95° C. (initial denaturing), 30 cycles of 45 seconds at 94° C., 45 seconds at 55° C. and 2 minutes at 72° C., followed by 5 minutes at 72° C. (final extension) and a final hold temperature of 10° C. The size, quality and quantity of the PCR product was evaluated by running a 5 uL aliquot on a 1% agarose gel, and comparing the product band to a mass ladder (Hi-Lo mass ladder, Bionexus, Oakland, Calif.).

1.2.3 16S rRNA Sequencing

Excess primers, nucleotides, enzyme and template were removed from the PCR product using the MoBio PCR clean up Kit (Cat No. 12500-50) following the manufacturer's instructions. The cleaned PCR product was subjected to direct sequencing using the primers described above.

1.2.4 Data Analysis

The forward and reverse sequences were aligned using the BioEdit software (http://www.mbio.nesu.edu/BioEdit/bioedit.html), and a consensus sequence was generated for further comparison to sequence databases. The identification of phylogenetic neighbors was initially carried out by the BLASTN (Altschul et al., 1997) program against the database containing type strains with validly published prokaryotic names and representatives of uncultured phylotypes (Kim et al., 2012). The top thirty sequences with the highest scores were then selected for the calculation of pairwise sequence similarity using global alignment algorithm (Myer & Miller, 1988), which was implemented at the EzTaxon-e server (http://extaxon-e.ezbiocloud.net/; Kim et al., 2012).

1.2.5 Results

The forward (SEQ ID NO:3) and reverse (SEQ ID NO:4) sequences were used to generate a 1445 base pair consensus sequence (SEQ ID NO:5).

The 16S rRNA gene consensus sequence of CL145A (ATCC 55799) was compared to those available sequences of type strains using EzTaxon-e server.

The search and comparison implements on Ex-Taxon-e server indicated that CL145A (also referred to as ATCC 55799 or MBI-401) was most similar to *Pseudomonas protegens* CHA0$^T$ and in comparison, more distantly related to *Pseudomonas fluorescens*. *Pseudomonas protegens* CHA0$^T$ is the type strain as described by Ramette et al., (2011).

Sequences were downloaded into MEGA5, and aligned using MUSCLE. A Neighbor-Joining tree was built to visualize the relationship of CL145A to the type strain of the genus *Pseudomonas* (FIG. 1). The tree clearly illustrates that CL145A is a strain of *Pseudomonas protegens*, and that *Pseudomonas fluorescens* falls in a more distant and separate branch of the tree.

The evolutionary history was inferred using the Neighbor-Joining method (Saitou and Nei, 1987). The bootstrap consensus tree inferred from 2000 replicates (Felsenstein, 1985) is taken to represent the evolutionary history of the taxa analyzed. Branches corresponding to partitions reproduced in less than 50% bootstrap replicates are collapsed. The percentage of replicate trees in which the associated taxa clustered together in the bootstrap test (2000 replicates) are shown next to the branches (Felsenstein, 1985). The tree is drawn to scale, with branch lengths in the same units as those of the evolutionary distances used to infer the phylogenetic tree. The evolutionary distances were computed using the Jukes-Cantor method (Jukes and Candor, 1969) and are in the units of the number of base substitutions per site. The analysis involved 21 nucleotide sequences. Codon positions included were 1st+2nd+3rd+Noncoding. All ambiguous positions were removed for each sequence pair. There were a total of 1505 positions in the final dataset. Evolutionary analyses were conducted in MEGA5 (Tamura et al., 2011).

Figure 2:
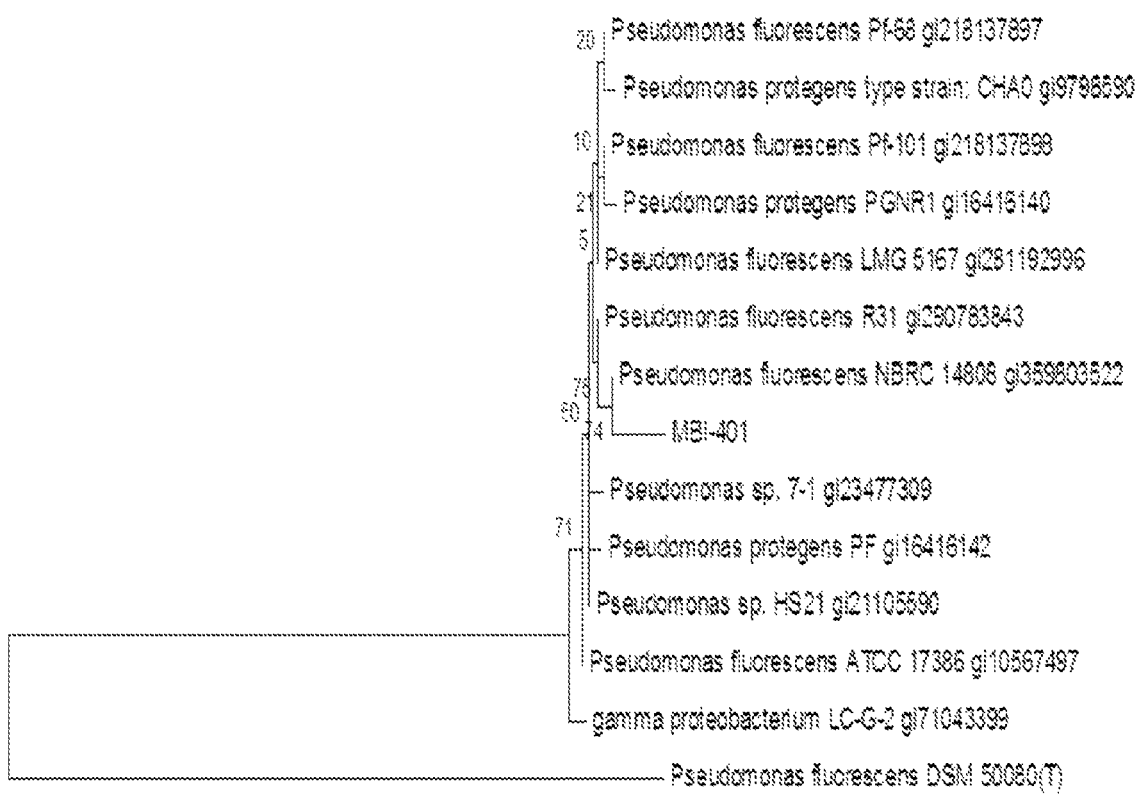
FIG. 2 shows the evolutionary relationships of taxa—A Neighbor-Joining Tree to visualize the relationship of CL145A (MBI-401) to the top matches to *Pseudomonas fluorescens* and *Pseudomonas protogens* from an NCBI BLAST search.

Additionally, comparisons were done with representatives of the bacterial domain using NCBI BLAST and limiting the search to the Reference Sequence Database. In order to confirm that the top matches from NCBI BLAST were actually due to misnaming of *Pseudomonas* isolates as *Pseudomonas fluorescens*, the top matches to *Pseudomonas fluorescens* (strains LMG 5167, Pf-101, Pf-68, CPF-10, 7-1, and LC-G-2) were compared to *Pseudomonas protegens* in Ez-Taxon to confirm that they were not incorrectly named in the NCBI BLAST database. The sequences were imported into MEGA5, aligned by MUSCLE against CL145A (MBI-401) and *Pseudomonas protegens* CHA0$^T$ and *Pseudomonas fluorescens* DSM 50080$^T$. A phylogenetic tree was constructed to evaluate taxonomy (FIG. 2). The phylogenetic tree shown in FIG. 2 illustrates that *Pseudomonas* strains LMG 5167, Pf-101, Pf-68, CPF-10, 7-1, and LC-G-2 were found to all match to *Pseudomonas protegens* type strain (CHA0$^T$), and that these strains were grouped together with *Pseudomonas protegens* strains in the phylogenetic tree. In contrast, the *Pseudomonas fluorescens* type strain (DSM$^T$) is not in the same group as the *Pseudomonas protegens* type strain (CHA0$^T$), as both strains are in different branches of the phylogenetic tree. The evolutionary history was inferred using the Neighbor-Joining method (Saitou and Nei, 1997). The bootstrap consensus tree inferred from 2000 replicates (Felsenstein, 1985) is taken to represent the evolutionary history of the taxa analyzed (Felsenstein, 1985). Branches corresponding to partitions reproduced in less than 50% bootstrap replicates are collapsed. The percentage of replicate trees in which the associated taxa clustered together in the bootstrap test (2000 replicates) are shown next to the branches (Felsenstein, 1985). The tree is drawn to scale, with branch lengths in the same units as those of the evolutionary distances used to infer the phylogenetic tree. The evolutionary distances were computed using the Jukes-Cantor method (Jukes and Cantor, 1969) and are in the units of the number of base substitutions per site. The analysis involved 14 nucleotide sequences. Codon positions included were 1st+2nd+3rd+Noncoding. All ambiguous positions were removed for each sequence pair. There were a total of 1515 positions in the final dataset. Evolutionary analyses were conducted in MEGA5 (Tamura et al., 2011).

1.3 Production of Pyoluteorin and 2,4-Diacetylphologlucinol

Ramette et al. (2011) describe the production of two secondary metabolites, pyoluteorin and 2,4-Diacetylphloroglucinol (DAPG), as a major characteristic differentiating *Pseudomonas protegens* from *Pseudomonas fluorescens* strains alongside genotypic and phenotypic characterization data. The fluorescent *Pseudomonas* type strain Pf-5 is known to produce both secondary metabolites, pyoluteorin and DAPG, and this strain was used as the positive control.

CL145A and Pf-5 strains were grown on pyoluteorin production broth enriched with 2% glycerol (PhGly), as described by Wang et al., (2011). The media contains per liter: 3 g NH$_4$NO$_3$, 1 g yeast extract, 1 g KH$_2$PO$_4$, 2 g NaCl, 0.5 g MgSO$_4$ and 1 ml of trace minerals solution. Fermentations were performed in 250 ml Erlenmeyer flasks with 50 ml of media. Incubation was performed at 25° C. and 200 rpm for 48 hours. Fermentations were done side-by-side with CL145A and Pf-5 (NRRL B-23932) and harvested after 48 hours. Due to the lack of commercially available standards for pyoluteorin, strain Pf-5 was used as an internal standard.

The fermentation broths were extracted using Amberlite XAD-7 resin (Asolkar et al., 2006) by shaking the Whole Cell Broth (WCB) with resin at 225 rpm for two hours at room temperature. The resin and cell mass were collected by filtration through cheesecloth and washed with deionized (DI) water to remove salts. The resin, cell mass, and cheesecloth were then soaked for 1 hour in acetone/methanol (1:1) after which the solvent was filtered and dried under vacuum using rotary evaporator to give the crude extract. The crude extracts obtained from the above were dissolved in methanol to get a known concentration (10 mg/mL) which were later analyzed using Liquid chromatography-mass spectrometry (LCMS).

Mass spectroscopy analysis of crude extract samples were performed on a Thermo Finnigan LCQ Deca XP Plus electrospray (ESI) instrument using both positive and negative ionization modes in a full scan mode (m/z 100-1500 Da) and on a LCQ DECA XPplus Mass Spectrometer (Thermo Electron Corp., San Jose, Calif.). Thermo high performance liquid chromatography (HPLC) instrument equipped with a Finnigan Surveyor PDA plus detector, autosampler plus, MS pump and a 4.6 mm×100 mm Luna C18 5 µm column (Phenomenex). The solvent system consisted of water (solvent A) and acetonitrile (solvent B). The mobile phase began at 10% solvent B and is linearly increased to 100% solvent B over 20 min and then kept for 4 min, and finally returned to 10% solvent B over 3 min and kept for 3 min. The flow rate was 0.5 mL/min. The injection volume was 10 µL and the samples were kept at room temperature in an auto sampler. Mass spectroscopy analyses of compounds of interest present in the samples were performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The compounds of interest in this analysis were pyoluteorin (1) and DAPG (2) which were characterized by comparing the UV absorbance profile, retention time (RT) and molecular weight with those of the internal reference standard compounds.

Pyoluteorin (1) and DAPG (2) have been reported as secondary metabolites from *Pseudomonas fluorescens* Pf-5 (Ramette et al., 2011). As a standard sample of pyoluteorin was not available, the crude extract of Pf-5 was used to identify the production of pyoluteorin in a crude extract of CL145A. Pyoluteorin has a RT of 11:30 min, a molecular mass of 272.02 in positive ionization mode and UV absorption max at 206, 254 & 308 nm. The isotopic spitting pattern in the MS confirms the presence of the two chlorine atoms in the molecule. The standard sample of 2,4-diacetylphloroglucinol (2) was purchased from Santa Cruz Biotechnology (CAS 2161-86-6) and has a RT of 13.99 min, molecular weight of 210.14 and UV absorption max at 204, 268 & 320 nm. The production of both the compounds 1 & 2 were detected with RT 11:30 and 13:96 min respectively in the crude extract of CL145A grown in the fermentation medium containing glycerol, with identical UV and mass spitting pattern to that of standard compounds. The structures for pyoluteorin and DAPG are shown in FIG. 3.

The production of both secondary metabolites pyoluteorin and DAPG by CL145A when grown under specific media, temperature and agitation conditions designed to optimize for the production of said metabolites. Presence of pyoluteorin was confirmed by identification of peaks according to mass spectrum patterns, retention times and UV spectra that are specific to pyoluteorin. The presence of DAPG was further confirmed by comparison to commercial standard.

Batches were produced in media FM3 and DM7 and analyzed as described above. Pyoluteorin and DAPG were not detected in these media under fermentation conditions typical of commercial manufacturing.

1.4 Conclusion

MBI-401, was conclusively identified as *Pseudomonas protegens* strain CL145A. An earlier effort to characterize the microorganism had yielded an identification of *Pseudomonas fluorescens* (Pf). The change in the species identity is the outcome of recent revisions to the taxonomy of *Pseudomonas fluorescens* that grouped several strains previous known as Pf into a new species characterized by divergence of 16S rRNA gene sequences and the production of pyoluteorin and DAPG, as well as other biochemical traits. Therefore, CL145A is now classified as a strain of the newly formed *Pseudomonas protegens* grouping.

Example 2: Preparation of *Pseudomonas* Fractions

Figure 4:
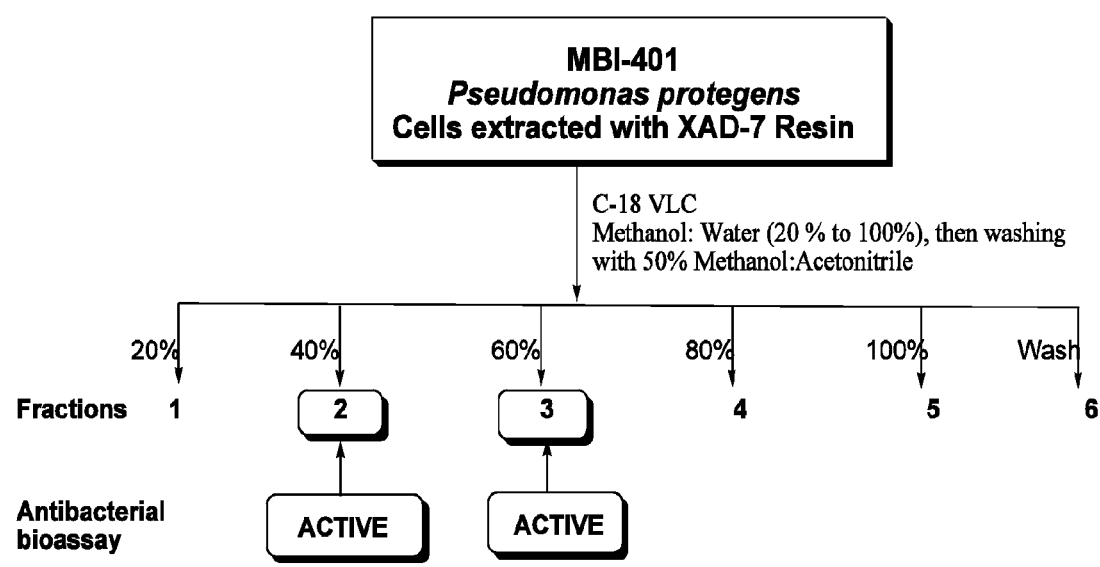
FIG. 4 shows the general scheme used to obtain fractions from the MBI-401 (cells extract) and bioassay results.

The following procedure is used for the extraction of compounds from the cells and supernatant of *Pseudomonas* CL145A (ATCC 55799):

The cell pellet derived from the 10-L fermentation P. CL145A (ATCC 55799) in FM2 growth medium is suspended in dilution buffer and extracted with Amberlite XAD-7 resin (Asolkar et al., 2006) by shaking the cell suspension with resin at 225 rpm for two hours at room temperature. The resin and cell mass are collected by filtration through cheesecloth and washed with DI water to remove salts. The resin, cell mass, and cheesecloth are then soaked for 2 h in acetone after which the acetone is filtered and dried under vacuum using rotary evaporator to give the crude extract. The crude extract is then fractionated by using reversed-phase C18 vacuum liquid chromatography ($H_2O$/ $CH_3OH$; gradient 90:20 to 0:100%) to give 6 fractions (see FIG. 4 for schematic).

2.1 Analysis of Active Fractions/Crude Extract

Figure 5:
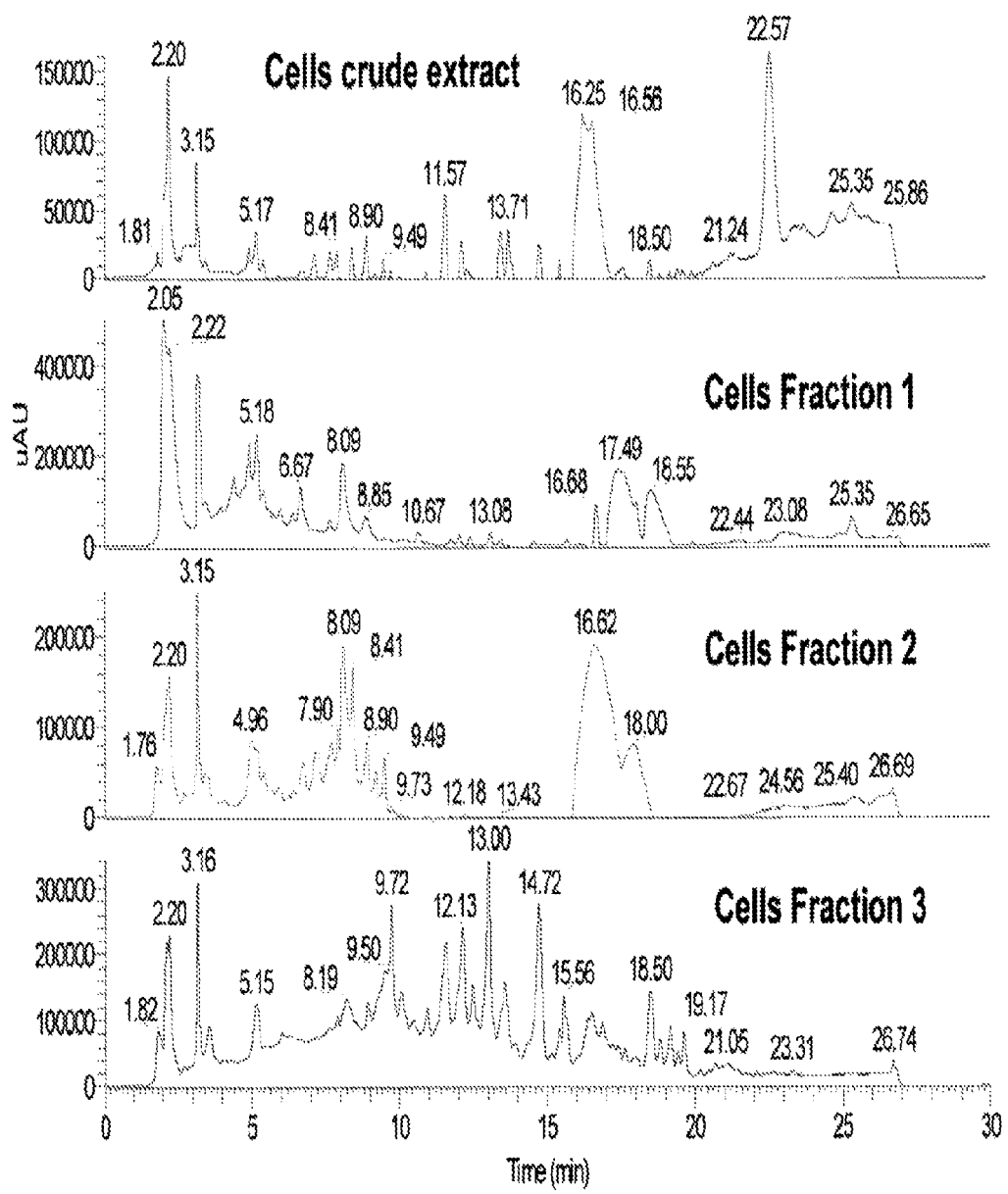
FIG. 5 shows a comparison of the active fractions 1, 2 and 3 to the crude extract as analyzed by reversed phase HPLC.
Figure 6:
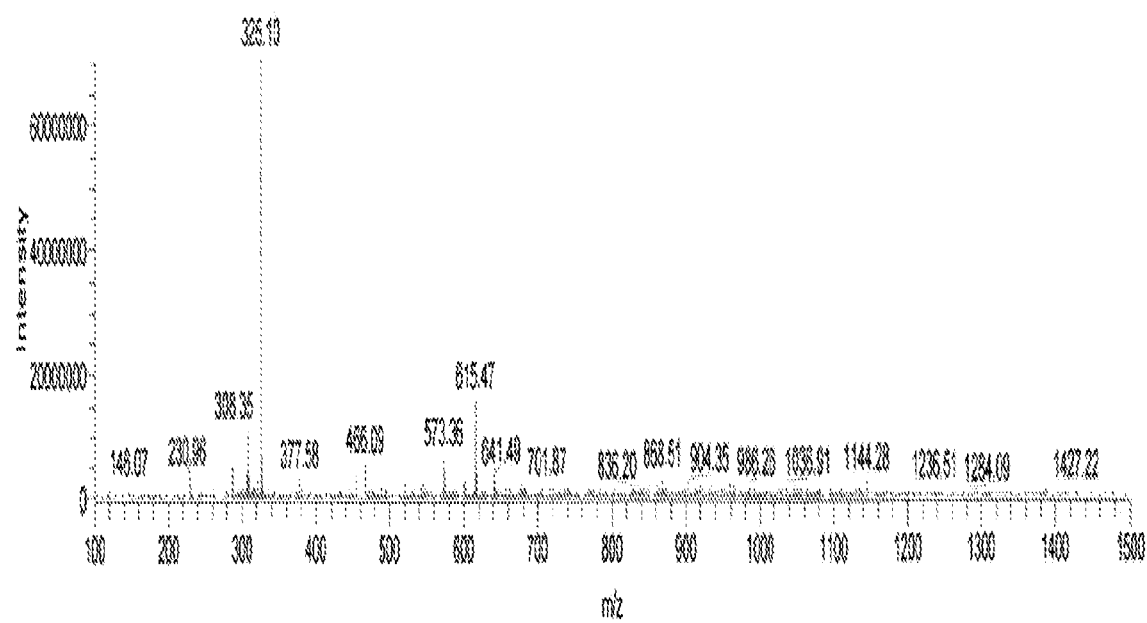
FIG. 6 shows the ESI MS analysis of the active fraction F1.
Figure 7:
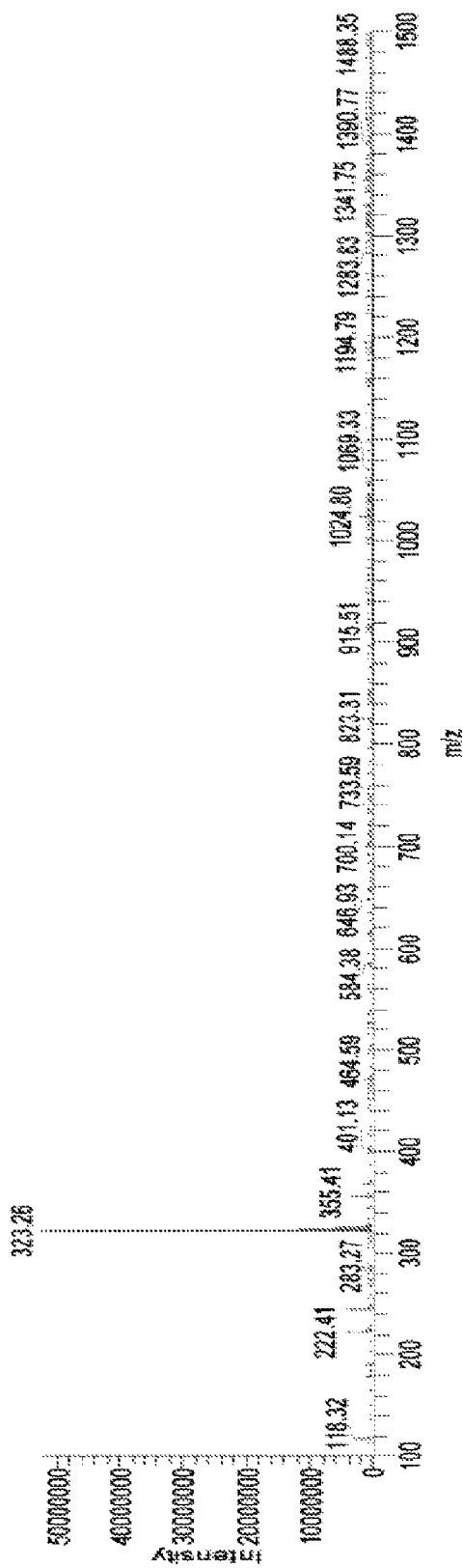
FIG. 7 shows the ESI MS analysis of the active fraction F2.
Figure 8:
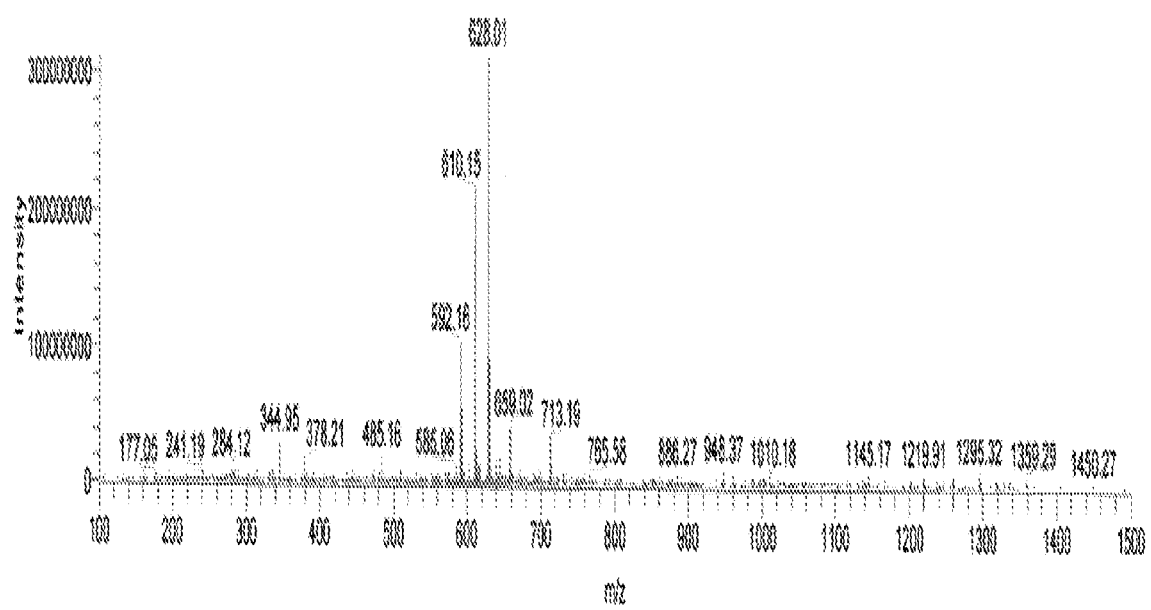
FIG. 8 shows the ESI MS analysis of the active fraction F3.
Figure 9:
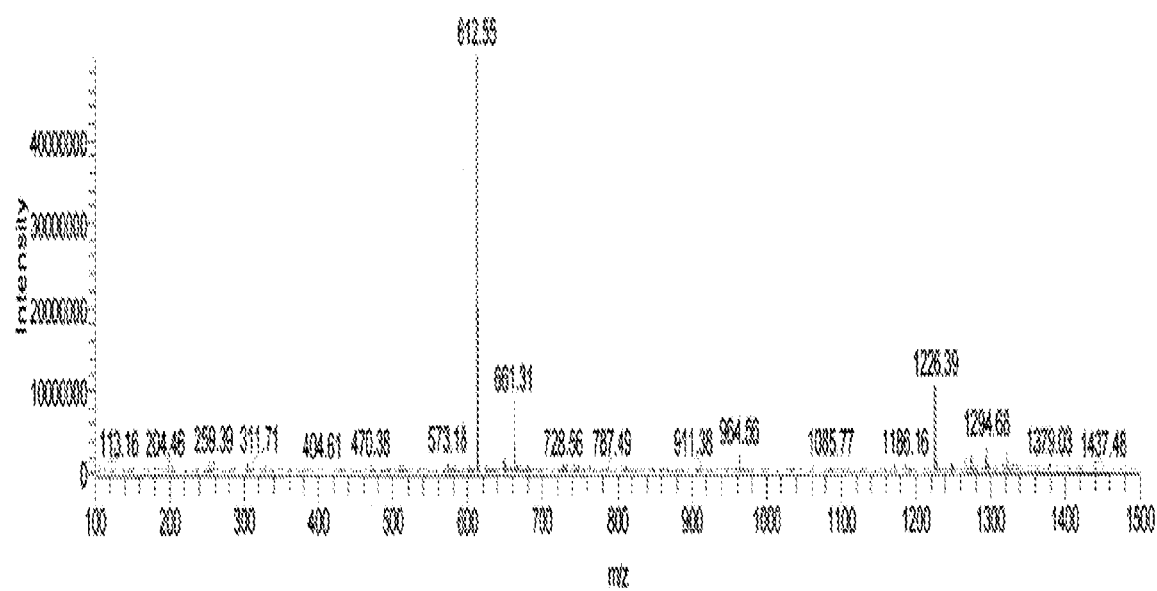
FIG. 9 shows ESI MS for crude extract obtained from the extraction of the supernatant (SN-XAD).

The comparison of the cells crude and the active fractions F1, F2 & F3 are shown in FIG. 5. These fractions are analyzed on a Thermo high performance liquid chromatography (HPLC) instrument equipped with Finnigan Surveyor PDA plus detector, autosampler plus, MS pump and a 4.6 mm×100 mm Luna C18 5 µm column (Phenomenex). The solvent system consisted of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume is 10 µL and the samples are kept at room temperature in an auto sampler. Further characterizations/analysis of the active fractions is shown in FIGS. 6, 7 and 8. Specifically, these fractions were analyzed using ESI-LCMS on a Thermo Finnigan LCQ Deca XP Plus electrospray (ESI) instrument using both positive and negative ionization modes in a full scan mode (m/z 100-1500 Da) on a LCQ DECA $XP^{plus}$ Mass Spectrometer (Thermo Electron Corp., San Jose, Calif.) and Thermo high performance liquid chromatography (HPLC) instrument equipped with Finnigan Surveyor PDA plus detector, autosampler plus, MS pump and a 4.6 mm×100 mm Luna C18 5 μm column (Phenomenex). The solvent system consisted of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume was 10 μL and the samples are kept at room temperature in an auto sampler. Mass spectroscopy analysis is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software.

The fractions F1, F2, F3 as well as the SN crude extract were analyzed using ESI-LCMS on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software.

Example 3: Antimicrobial Testing: Growth Inhibition on Agar Plate

*Pseudomonas* strain CL145A was streaked on a PDA plate by spreading glycerol stock material as a single straight line across the diameter of the plate. The strain CL145A was allowed to grow for 24 hours at 25° C. After 24 hours incubation, the following isolates were inoculated in perpendicular line to the CL145A growth, coming as close as possible to the CL145A growth without touching it: *Xanthomonas campestris, Xanthomonas vesicatoria, Pseudomonas putida, Bacillus cereus, Bacillus subtilis* and *Pseudomonas syringae*. The plate was incubated for another 48 hours at 25° C. Inhibitory activity was determined by looking for lack of growth in proximity to the CL145A streak. Isolates inhibited did not grow toward the CL145 streak; *X. campestris, X. vesicatoria* and *B. subtilis* were significantly inhibited on the plate. *Pseudomonas putida* was not inhibited at all. Minimal inhibition of *Bacillus cereus* was observed. *Pseudomonas syringae* grew poorly, but the results regarding inhibition due to CL145A were inconclusive.

Example 4: Antimicrobial Testing of Fractions Using Agar-Disc Assays

Plant pathogens were plated on PDA and incubated until enough biomass grew on the plate surface, usually 24-48 hours at 25° C. Then 1 mL of sterile water was inoculated with a loopful of the test microbe previously grown on PDA plates. The colony was resuspended in the sterile water and 200 μL of the pathogen resuspension was spread onto a PDA plate and left to be absorbed into the plate for 10-15 minutes. For testing against *Botrytis cinerea*, a plug of the fungus was placed in the middle of a PDA plate and left to incubate at 25° C. for 24 hours. Sterile filter discs were applied to the agar and were loaded with 20 μL of each of the samples prepared in methanol at 10 mg/mL. The plates were incubated at 25° C. for 48 hours. After 48 hours the plates were observed for a zone of inhibition around the filter discs, indicating pathogen resistance to the sample. Inhibition is indicated by a zone of inhibition around the filter paper discs. CL145A extracts and fractions were tested against: (A) *Xanthomonas campestris*, (B) *Xanthomonas arboricola*, (C) *Xanthomonas vescictoria*, (D) *Bacillus subtilis*, (E) *Steptomyces scabiei*, (F) *Erwinia carotovora*, (G) *Bacillus cereus* and (H, I) *Botrytis cinerea*. Results are summarized in Table 5.

The results from these studies indicate that CL145A whole cell broth, cells, extracts and fractions were found to display inhibitory activity against an array of microorganisms involved in plant disease. Different fractions displayed activity against different microorganisms, indicating Pf145A has the potential to producing a diverse number of metabolites with varying antibacterial activity. Activity was found in both the supernatant and whole cell broth, indicating active metabolites might be both cell-bound and extracellular in nature. However, Fraction 3 was found to have activity against all microorganisms tested.

TABLE 5

| fCL145A sample description | Bacillus subtilis ATCC 21331 | Bacillus cereus | Xanthomonas campestris ATCC 33442 | Xanthomonas arboricola ATCC 11329 | Xanthomonas vesicatoria ATCC 35937 | Streptomyces scabiei ATCC 49173 | Erwinia carotovora | Botrytis cinerea |
|---|---|---|---|---|---|---|---|---|
| 401-Cells-F1 | − | +++ | + | +++ | − | ++ | +++ | − |
| 401-Cells-F2 | +++ | +++ | + | + | − | +++ | +++ | − |
| 401-Cells-F3 | +++ | +++ | + | ++ | +++ | +++ | +++ | +++ |
| 401-Cells-F4 | ++ | ++ | + | ++ | − | +++ | +++ | +++ |
| 401-Cells-F5 | − | ++ | ++ | + | ++ | ++ | ++ | ++ |
| 401-Cells-F6 | − | − | + | − | − | ++ | +++ | − |
| 401-Cells CE | − | +++ | ++ | + | + | +++ | +++ | ++ |
| 401-SN/XAD | +++ | +++ | + | +++ | +++ | +++ | +++ | ++ |
| 401-WCB/XAD | ++ | +++ | +++ | + | + | +++ | +++ | +++ |
| 401-SN-aq/EA | − | ++ | + | ++ | − | − | ++ | ++ |
| 401-WCB-aq/EA | − | ++ | + | + | − | − | ++ | − |

Example 5: The Effect of MBI-401 on Cucumber Plants Infected with Powdery Mildew Two-week old cucumber plants (*C. sativus*) were thoroughly sprayed (to the point of run-off when the solution almost to drip off leave surface) with MBI-401 whole cell broth (n=7) and supernatant (n=7), water was used as a negative control (n=6). Application was done with a hand-held pressurized sprayer to simulate a commercial fungicide treatment performed in greenhouse vegetable production systems. Volume applied was 3 mL of spray volume per plant. Plants were allowed to dry before being inoculated with a spore suspension of *S. fulginea*, the causative agent of powdery mildew. The spore suspension was sprayed to the point of runoff onto the treated and untreated plants. Use 2 mL of conidia suspension spray volume per plant. The treated and untreated plants were incubated at approximately 22° C. (Temperature range for sporulation is from 15° C. to 30° C.), until the disease severity reach at least 90%, ideally 100% on the water control in about 7 to 14 days. Disease severity was evaluated by assessing percentage leaf area covered with colonies on all treated and untreated plants 10 DAT.

Figure 10:
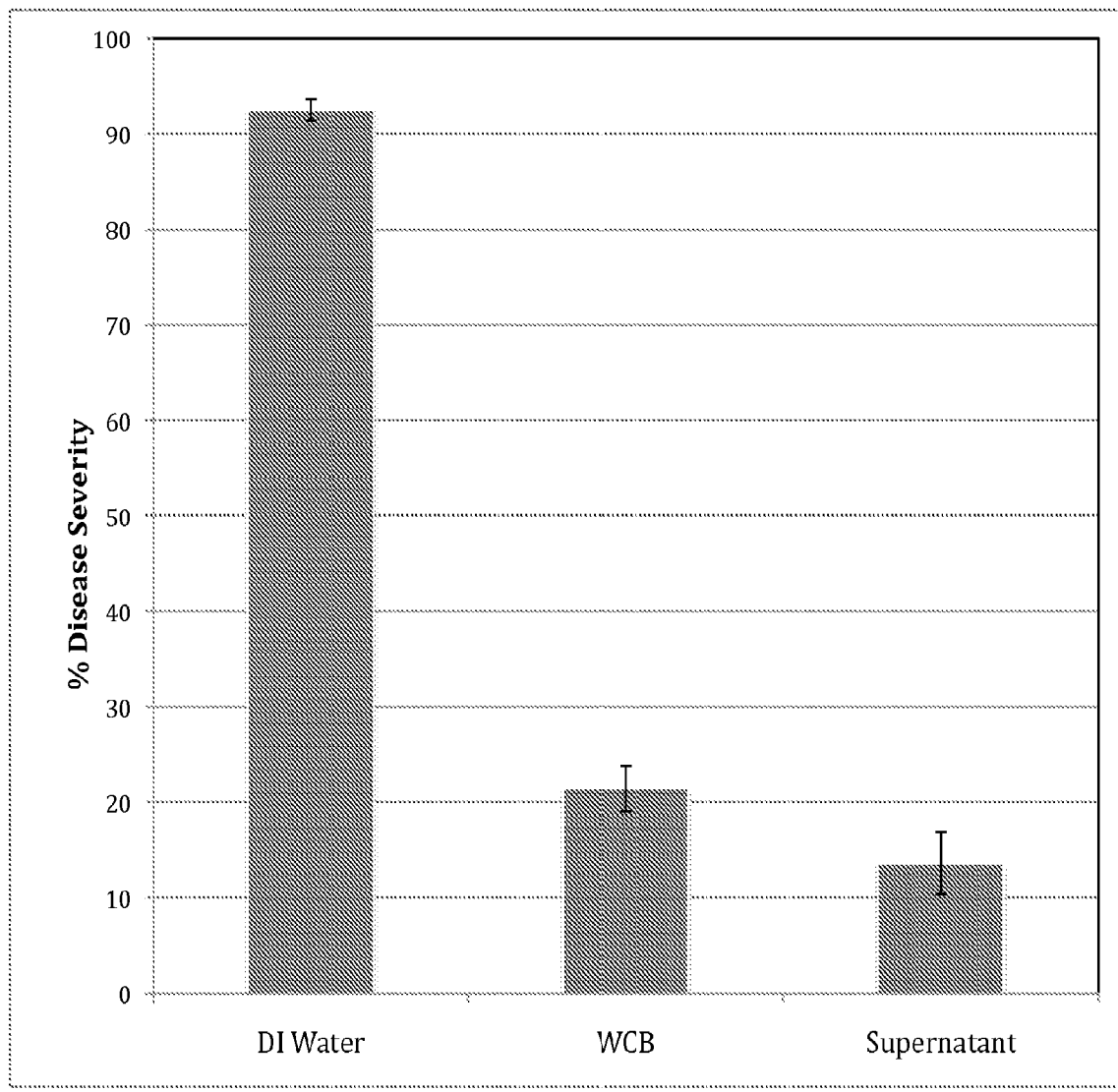
FIG. 10 shows the effect of MBI-401 on Cucumber Plants Infected with Powdery Mildew.

The results are shown in FIG. 10. Plants treated with whole-cell broth and supernatant presented significantly reduced ($p<0.005$, ANOVA) disease severity (approx. 15-20%) compared to the untreated plants (approx. 90% severity).

REFERENCE LIST

Altschul, S. F., Madden, T. L., Schaeffer, A. A., Zhang, J., Zhang, Z., Miller, W. & Lipman, D. J. (1997). Gapped BLAST and PSI-BLAST: a new generation of protein database search programs. Nucleic Acids Res 25, 3389-3402.
Asolkar R N, Jensen P R, Kauffman C A, Fenical W., Daryamides A-C, (2006). Weakly Cytotoxic Polyketides from a Marine-Derived Actinomycete of the Genus *Streptomyces* Strain CNQ-085. Journal of Natural Products 69:1756-1759.
Brenner et al. Editors, Garrity G. M. Ed-in-Chief. Springer Jukes T. H. and Cantor C. R. (1969). Evolution of protein molecules. In Munro H N, editor, Mammalian Protein Metabolism, pages 21-132. Academic Press, New York.
Dowling and O'Gara. (1994). Metabolites of *Pseudomonas* involved in the biocontrol of plant disease. TIBTECH 12:133-141.
Euzeby, J. (2012). List of new names and mew combinations previously effectively, but not validly, published. International Journal of Systematic and Evolutionary Microbiology. 62:1443-1445.
Felsenstein J. (1985). Confidence limits on phylogenies: An approach using the bootstrap. Evolution. 39, pages 783-791.
Keel, C., Schnider, M. M., Voisard, C., Laville, J., Burger, U., Wirthner, P., Haas, D. and DHagoi, G. (1992). Suppression of Root Diseases by *Pseudomonas fluorescens* CHAO: Importance of the Bacterial Secondary Metabolite 2,4-Diacetylphloroglucinol. Mol. Plant-Microbe Interactions 5:4-13.
Kim, O. S., Cho, Y. J., Lee, K., Yoon, S. H., Kim, M., Na, H., Park, S. C., Jeon, Y. S., Lee, J. H., Yi, H., Won, S., Chun, J. (2012). Introducing EzTaxon-e: a prokaryotic 16S rRNA Gene sequence database with phylotypes that represent uncultured species. Int J Syst Evol Microbiol 62, 716-721.
Myers, E. W. & Miller, W. (1988). Optimal alignments in linear space. Comput Appl Biosci 4, 11-17.
Palleroni, N. J. (2005). Genus *Pseudomonas*. In: Bergey's Manual of Systematic Bacteriology. $2^{nd}$ Ed. Volume Two: The Proteobacteria Part B The Gammaproteobacteria. Pages 323-379.
Ramette, A., Frapoli, M., Fischer-Le Saux, M., Gruffaz, C., Meyer, J-M., Defago, G., Sutra, L and Moenne-Loccoz, Y. (2011). *Pseudomonas protegens* sp. Nov., widespread plant-protecting bacteria producing the biocontrol compounds 2,4-diacetylphloroglucinol and pyoluteorin. Systematic and Applied Microbiology. 34, pages 180-188.
Saitou N. and Nei M. (1987). The neighbor joining method: A new method for reconstructing phylogenetic trees. Molecular Biology and Evolution. 4, pages 406-425.
Tamura K., Peterson D., Peterson N., Stecher G., Nei M., and Kumar S. (2011). MEGA5: Molecular Evolutionary Genetics Analysis using Maximum Likelihood, Evolutionary Distance, and Maximum Parsimony Methods. Molecular Biology and Evolution (In Press).
U.S. Pat. Nos. 6,194,194, 5,622,846, 5,552,315
Wang, W., Dong, H., Zhang, J., Xu, Y., and Xang, X. (2011). Chapter 5. The production, separation and stability of pyoluteorin: a biological perspective. In: Pesticides in the Modern world—Pests control and pesticides exposure and toxicity assessment. Margarita Stoytcheva, Ed. 614 pages. Published by InTech.

This invention may be embodied in other forms or carried out in other ways without departing from the spirit or essential characteristics thereof. The present disclosure is therefore to be considered as in all aspects illustrate and not restrictive, and all changes which come within the meaning and range of equivalency are intended to be embraced therein.

Various references are cited throughout this specification, each of which is incorporated herein by reference in its entirety.

What is claimed is:

1. A method of inhibiting one or more phytopathogenic microorganisms in a location comprising the step of: introducing into said location an amount of a cell suspension, supernatant, filtrate, cell fraction, or whole cell broth derived from a *Pseudomonas* ATCC55799, effective to inhibit said phytopathogenic microorganisms; wherein said location is in the soil, and said one or more phytopathogenic microorganisms is selected from the group consisting of *Bacillus subtillus, Bacillus cereus, Xanthomonas campestris, Xanthamonas arboricola, Xanthamonas vesicatoria, Streptomyces scabie, Botrytis cinerea, Erwinia carotovora*, and *Sphaerotheca fulginea*.

2. The method according to claim 1, wherein said method further comprises introducing another anti-microbial agent into said location.

3. The method of claim 1, wherein said location comprises plant parts.

* * * * *